US009536047B2

(12) United States Patent
Ayday et al.

(10) Patent No.: US 9,536,047 B2
(45) Date of Patent: *Jan. 3, 2017

(54) PRIVACY-ENHANCING TECHNOLOGIES FOR MEDICAL TESTS USING GENOMIC DATA

(71) Applicant: Ecole Polytechnique Federale De Lausanne (EPFL), Lausanne (CH)

(72) Inventors: Erman Ayday, Ankara (TR); Jean-Pierre Hubaux, St-Sulpice (CH); Jean L. Raisaro, Lausanne (CH); Amalio Telenti, La Jolla, CA (US); Jacques Fellay, St. Maurice (CH); Paul J. McLaren, Winnipeg (CA); Jacques Rougemont, Geneva (CH); Mathias Humbert, Saarbrücken (DE)

(73) Assignee: Ecole Polytechnique Federale de Lausanne (EPFL) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/993,840

(22) Filed: Jan. 12, 2016

(65) Prior Publication Data
US 2016/0224735 A1 Aug. 4, 2016

Related U.S. Application Data

(63) Continuation-in-part of application No. 14/428,285, filed as application No. PCT/EP2013/068658 on Sep. 10, 2013, now Pat. No. 9,270,446.
(Continued)

(30) Foreign Application Priority Data

Sep. 14, 2012 (EP) ..................... 12184372

(51) Int. Cl.
G06F 11/30 (2006.01)
G06F 12/14 (2006.01)
(Continued)

(52) U.S. Cl.
CPC ............. *G06F 19/322* (2013.01); *G06F 19/18* (2013.01); *G06F 21/6245* (2013.01);
(Continued)

(58) Field of Classification Search
CPC ............. H04L 9/08; H04L 9/14; H04L 9/0819
(Continued)

(56) References Cited

U.S. PATENT DOCUMENTS

2010/0121872 A1* 5/2010 Subramaniam ......... G06F 19/28
707/769

OTHER PUBLICATIONS

Erman Ayday: Privacy-Enhancing Technologies for Medical Tests Using Genomic Data, Dec. 28, 2012; p. 16.*
(Continued)

Primary Examiner — Evans Desrosiers
(74) Attorney, Agent, or Firm — Blank Rome LLP

(57) ABSTRACT

In this invention, we propose privacy-enhancing technologies for medical tests and personalized medicine methods, which utilize patients' genomic data.
Assuming the whole genome sequencing is done by a certified institution, we propose to store patients' genomic data encrypted by a patient's public keys at a Storage and Processing Unit (SPU). A part of the corresponding private key is also stored on the SPU. At the time of the test by a Medical Unit (MU), the patient provides the second part of the private key to the MU. A test with its associated markers is determined by the MU and sent to the SPU. The test is carried out on the encrypted values thanks to homomorphic operation and returned back to the MU. The latter uses the second part of the private key to access the result.

8 Claims, 6 Drawing Sheets

Related U.S. Application Data

Figure 1:
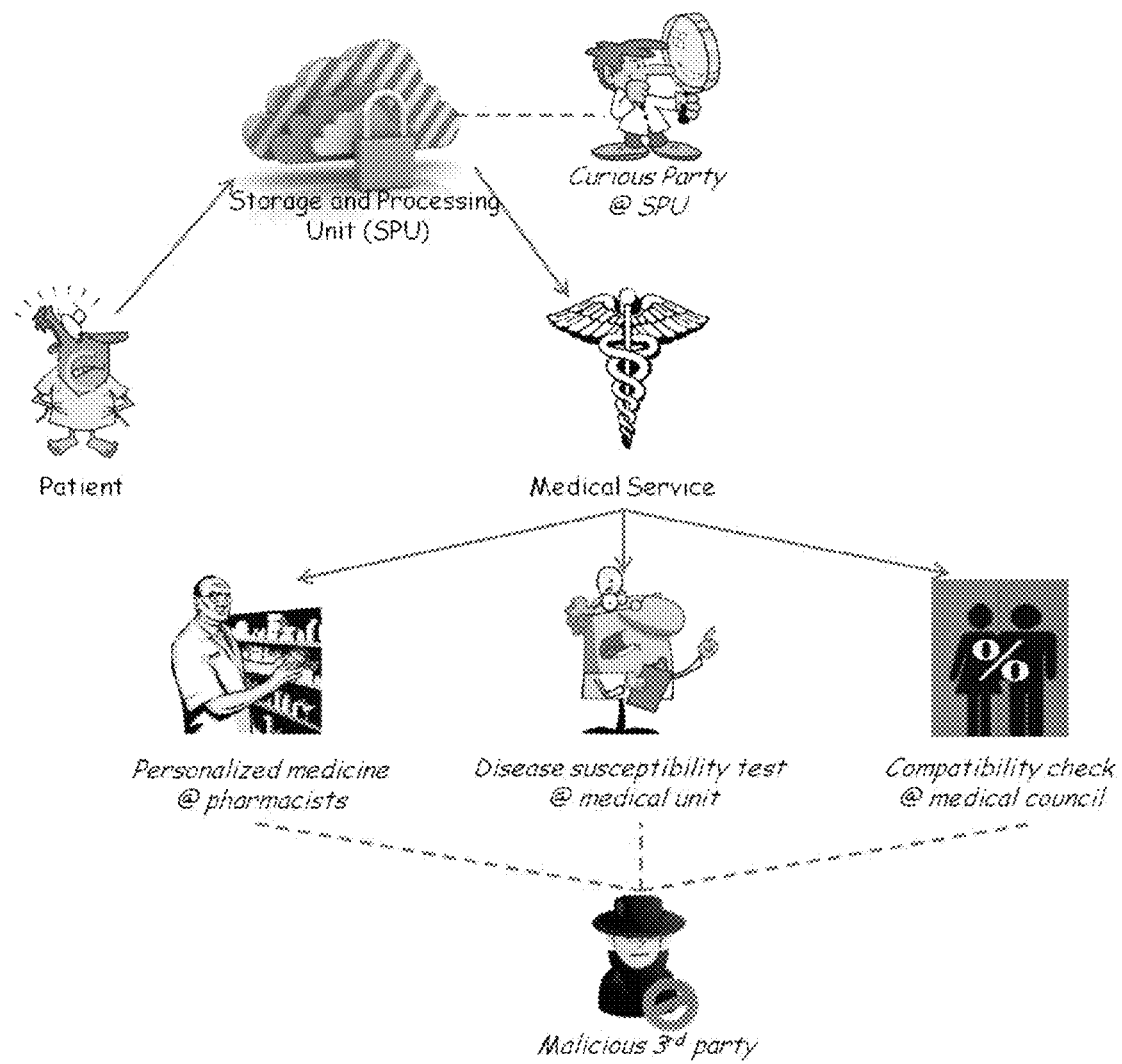

(60) Provisional application No. 61/700,897, filed on Sep. 14, 2012.

(51) Int. Cl.

| | | |
|---|---|---|
| G06F 19/00 | (2011.01) | |
| G06F 19/18 | (2011.01) | |
| H04L 9/14 | (2006.01) | |
| H04L 9/08 | (2006.01) | |
| G06F 21/62 | (2013.01) | |
| H04N 7/167 | (2011.01) | |

(52) U.S. Cl.
CPC .............. *H04L 9/0866* (2013.01); *H04L 9/14* (2013.01); *G06Q 2220/10* (2013.01)

(58) Field of Classification Search
USPC ......... 713/182–186, 202; 709/206, 225, 229, 709/249, 389; 726/2–8
See application file for complete search history.

(56) References Cited

OTHER PUBLICATIONS

Kantarcioglu M: Cryptographic Approach to Securely Share and Query Genomic Sequences Sep. 1, 2008; pp. 606-617.*
International Search Report issued PCT/EP2013/068658 dated Feb. 26, 2014.
Written Opinion issued PCT/EP2013/068658 dated Feb. 26, 2014.
Erman Ayday et al., "Privacy-Enhancing Technologies for Medical Tests Using Genomic Data", retrieved from http://infoscience.epfl.ch/record/182897_/files/cs_version_techn_ical_report.pdf, dated Dec. 28, 2012 (16 pages).
Murat Kantarcioglu et al., "A Cryptographic Approach to Securely Share and Query Genomic Sequences", IEEE Transactions on Information Technology in Biomedicine, vol. 12, No. 5, pp. 606-617, Sep. 2008.
Thomas Neubauer et al., "A Methodology for the Pseudonymization of Medical Data", International Journal of Medical Informatics, vol. 80, pp. 190-204 (2011 ).
Stefanos Gritzalis et al., "Technical Guidelines for Enhancing Privacy and Data Protection in Modern Electronic Medical Environments", IEEE Transactions on Information Technology in Biomedicine, vol. 9, No. 3, pp. 413-423, Sep. 2005.
Ann Cavoukian, "Privacy by Design", Information and Privacy Commissioner of Ontario, http://vvww.ontla.on.ca/library/repository/mon/23002/289982.pdf, Jan. 2009 (4 pages).
Fahriye Seda Gurses, "Multilateral Privacy Requirments Analysis in Online Social Network Services", PhD Thesis Katholieke Universiteit Leuven, Arenberg Doctoral School of Science, Engineering and Technology, May 2010 (312 pages).
Marc Langheinrich, "Privacy by Design—Principles of Privacy-Aware Ubiquitous Systems", In Ubicomp 2011: Ubiquitous Computing, pp. 273-291 (2001 ).
G.W. van Blarkom et al., "Handbook of Privacy and Privacy-Enhancing Technologies: The Case of Intelligent Software Agents", PISA (Privacy Incorporated Software Agent), College Bescherming Persoonsgefevens, Copyright 2003, (372 pages).
George M. Church, "Consent Form: Personal Genome Project", Harvard Medical School, Feb. 18, 2014 (24 pages).
Juan Ramon Troncoso-Pastoriza et al., "Privacy Preserving Error Resilient DNA Searching Through Oblivious Automata", CCS'07, pp. 519-528, Oct. 29-Nov. 2, 2007.
Marina Blanton et al., "Secure Outsourcing of DNA Searching Via Finite Automata", IFIP International Federation for Information Processing 2010: Data and Applications Security XXIV, LNCS 6166, pp. 49-64 (2010).
Somesh Jha et al., "Towards Practical Privacy for Genomic Computation", Proceedings of the 2008 IEEE Symposium on Security and Privacy, pp. 216-230 (2008).
Fons Bruekers et al., "Privacy-Preserving Matching of DNA Profiles", Technical Report, May 8, 2008 (16 pages).
Pierre Baldi et al., "Countering GATTACA": Efficient and Secure Testing of Fully-Sequenced Human Genomes (Full Version), CCS'11: Proceedings of the $18^{th}$ ACM Conference on Computer and Communications Security, pp. 691-702 (2011).
Mustafa Ganim et al., "Secure Management of Biomedical Data with Cryptographic Hardware", IEEE Transactions on Information Technology in Biomedicine, vol. 16, No. 1, pp. 166-175, Jan. 2012.
David Eppstein et al., "Privacy-Enhanced Methods for Comparing Compressed DNA Sequences", Printed from http://arxiv.org/abs/1107.3593 (17 pages) (2011).
David Eppstein et al., "Straggler Identification in Round-Trip Data Streams Via Newton's Identities and Invertible Bloom Filters", IEEE Transactions on Knowledge and Data Engineering, vol. 32, No. 2, pp. 297-306 (2011).
Rui Wang et al., "Learning Your Identity and Disease from Research Papers: Information Leaks in Genome Wide Association Study", CCS'09: Proceedings of the 16th ACM Conference on Computer and Communications Security, pp. 534-544, Nov. 9-13, 2009.
Bradley Malin et al., "How (Not) to Protect Genomic Data Privacy in a Distributed Network: Using Trail Re-Identification to Evaluate and Design Anonymity Protection Systems", Journal of Biomedical Informatics, vol. 37, pp. 179-192 (2004).
Nils Homer et al., "Resolving Individuals Contributing Trace Amounts of DNA to Highly Complex Mixtures Using High-Density SNP Genotyping Microarrays", PLOS Genetics, vol. 4, No. 8, pp. 1-9, Aug. 2008.
Jane Gitschier, "Inferential Genotyping of Y Chromosomes in Latter-Day Saint Founders and Comparison to Utah Samples in the HapMap Project", The American Journal of Human Genetics, vol. 84, pp. 251-258, Feb. 13, 2009.
Xiaoyong Zhou et al., "To Release or Not to Release: Evaluating Information Leaks in Aggregate Human-Genome Data", Presentation as ESORICS, 2011 (31 pages), (2011 ).
Stephen E. Fienberg et al., "Privacy Preserving Gwas Data Sharing", IEEE $11^{th}$ International Conference on Data Mining Workshops (ICDMW), pp. 628-635 (2011 ).
Yangyi Chen et al., "Large-Scale Privacy-Preserving Mapping of Human Genomic Sequences on Hybrid Clouds", NOSS, (18 pages) (2012).
Rui Wang et al., "Privacy-Preserving Genomic Computation Through Program Specialization", CCS'09: Proceedings of the 16th ACM Conference on Computer and Communications Security, pp. 338-347, Nov. 9-13, 2009.
Rakesh Agrawal et al., "Information Sharing Across Private Databases", SIGMOD 2003, Jun. 9-13, 2003 (12 pages).
Dana Dachman-Soled et al., "Efficient Robust Private Set Intersection", ANCS 2009, LNCS 5536, pp. 125-142 (2009).
Sekar Kathiresan et al., "Polymorphisms Associated with Cholesterol and Risk of Cardiovascular Events", The New England Journal of Medicine, vol. 358, No. 12, pp. 1240-1249, Mar. 20, 2008.
Evan A. Ashley et al., "Clinical Assessment Incorporating a Personal Genome", Lancet, vol. 375, pp. 1525-1535, May 1, 2010.
Sudha Seshadri et al., "Genome-Wide Analysis of Genetic Loci Associated with Alzheimer Disease", Jama, vol. 303, No. 18, pp. 1832-1840, May 12, 2010.
"dbSNP: Short Genetic Variation", printed from http://ncbi.nlm.nih.qov/projects/SNP/ on Apr. 9, 2015 (2 pages).
Dov Greenbaum et al., "Genomics and Privacy: Implications of the new Reality of Closed Data for the Field", PLOS Computational Biology, vol. 7, No. 12, pp. 1-6, Dec. 2011.
Mariana Raykova et al., "Privacy Enhanced Data Control for Outsourced Data Sharing", Financial Cryptography and Data Security, LNCS 7397, pp. 223-238 (2012).
Michael T. Goodrich et al., "Privacy-Preserving Access of Outsourced Data Via Oblivious RAM Simulation", Proceedings of the 38th International Conference on Automata, Lanquaqes and Programming, vol. Part II, pp. 576-587 (2011).
Emil Stefanov et al., "Towards Practical Oblivious RAM", Proceeding of the $19^{th}$ Network and Distributed Systems Security Symposium (NDSS'12) (40 pages) (2012).

(56) References Cited

OTHER PUBLICATIONS

Emmanuel Bresson et al., "A Simple Public-Key Cryptosystem with a Double Trapdoor Decryption Mechanism and its Applications", Proceedings of the Asiacrypt 03, LNCS 2894, pp. 37-54 (2003).

Matthew Pirretti et al., "Secure Attribute-Based System", Proceedings of the 13$^{th}$ ACM Conference on Computer and Communications Security (CCS'06), Oct. 30-Nov. 3, 2006 (14 pages).

Giusepe Ateniese et al., "Improved Proxy Re-Encryption Schemes with Applications to Secure Distributed Storage", ACM Transactions on Information and System Security, vol. 9, pp. 1-30, Feb. 2006.

D.S. Falconer et al., "Perspectives: Anecdotal, Historical and Critical Commentaries on Genetics", Genetics, vol. 167, pp. 1529-1536, Aug. 2004.

C. Diaz et al., "Towards Measuring Anonymity", presentation from Proceedings of Privacy Enhancing Technologies Symposium (PETS'02) (14 pages) (2002).

Andrei Serjantov et al., "Towards an Information Theoretic Metric for Anonymity", Proceedings of Privacy Enhancing Technologies Symposium (PETS'02) (14 pages) (2002).

Burton H. Bloom, "Space/Time Trade-Offs in Hash Coding with Allowable Errors", Communications of the ACM, vol. 13, No. 7, pp. 422-426, Jul. 1970.

Fang Hao et al., "Building High Accuracy Bloom Filters Using Partitioned Hashing", SIGMETRICS'07, pp. 277-287, Jun. 12-16, 2007.

Paulo Sergio Almeida et al., "Scalable Bloom Filters", Information Processing Letters, vol. 101, No. 6, pp. 255-261 (2007).

Richard M. Durbin et al., "A Map of Human Genome Variation from Population-Scale Sequencing", Nature, vol. 467, pp. 1061-1073, Oct. 28, 2010.

\* cited by examiner

PRIVACY-ENHANCING TECHNOLOGIES FOR MEDICAL TESTS USING GENOMIC DATA

RELATED APPLICATIONS

This application is a continuation-in-part of U.S. patent application Ser. No. 14/428,285, based on PCT application PCT/EP2013/068658, filed on Sep. 10, 2013, which claims priority of European Patent Application EP12184372.6. The content of all those applications is hereby enclosed by reference.

INTRODUCTION

The present invention relates to personalized medicine. More specifically, the present invention concerns a privacy-preserving method for performing disease susceptibility tests on a patient.

In this application, we propose privacy-enhancing technologies for medical tests and personalized medicine methods, which utilize patients' genomic data. First, we highlight the potential privacy threats on genomic data and the challenges of providing privacy-preserving algorithms. Then, focusing specifically on a typical disease-susceptibility test, we develop a new architecture (between the patient and the medical unit) and propose privacy-preserving algorithms.

1 BACKGROUND ART

Privacy control can be defined as the ability of individuals to determine when, how, and to what extent information about themselves is revealed to others. In this way, the usage of private data will remain in context and it will be used exclusively for the purpose the data owner has in mind. Privacy is usually protected by both legal and technological means. By using legal actions, such as data protection directives and fair information practices, privacy regulations can enforce privacy protection on a large scale. Yet, this approach is mostly reactive, as it defines regulations after technologies are put in place. To avoid this issue, Privacy-Enhancing Technologies (PETs) [1-3] can be incorporated into the design of new systems in order to protect individuals' data. PETs protect privacy by eliminating or obfuscating personal data, thereby preventing misuse or involuntary loss of data, without affecting the functionality of the information system [4].

Their objective is to make it difficult for a malicious entity to link information to specific users. In order to obfuscate personal data, PETs often rely on cryptographic primitives, such as anonymous authentication and encryption.

Genomics is becoming the next significant challenge for privacy. The price of a complete genome profile has plummeted below $200 for genome-wide genotyping (i.e., the characterization of about one million common genetic variants), which is offered by a number of companies (located mostly in the US). Whole genome sequencing is also offered through the same direct-to-consumer model (but at a higher price). This low cost of DNA sequencing will break the physician/patient connection, because private citizens (from anywhere in the world) can have their genome sequenced without involving their family doctor. This can open the door to all kinds of abuse, not yet fully understood.

As a result of the rapid evolution in genomic research, substantial progress is expected in terms of improved diagnosis and better preventive medicine. However, the impact on privacy is unprecedented, because (i) genetic diseases can be unveiled, (ii) the propensity to develop specific diseases (such as Alzheimer's) can be revealed, (iii) a volunteer accepting de facto to have his genomic code made public (as it already happened) can leak substantial information about his ethnic heritage and genomic data of his relatives (possibly against their will), and (iv) complex privacy issues can arise if DNA analysis is used for criminal investigations and insurance purposes. Such issues could lead to genetic discrimination (e.g., ancestry discrimination or discrimination due to geographic mapping of people). Even though the Genetic Information Non-discrimination Act (GINA), which prohibits the use of genomic information in health insurance and employment, attempted to solve some of these problems in the US, these types of laws are very difficult to enforce.

An even more severe case, currently not widely considered, is where a malicious party initiates a cross-layer attack by utilizing privacy-sensitive information belonging to a person retrieved from different sources (e.g., genomic data, location, online social network, etc.), thus creating the opportunity for a large variety of fraudulent uses of such data. For example, as stated in the Personal Genome Project (PGP) consent form [5], a malicious party could make synthetic DNA of a person and plant it at a crime scene to falsely accuse him.

In this hypothetical situation, the attacker can make his accusation stronger if he has the location patterns of the person to be blamed, and hence, knows that the person was close to the crime scene at the time of the crime. Similarly, an attacker can easily obtain information on close relatives of a target from online social network data, thus effectively increasing the potential access to target's genomic data if his relatives' DNA has been sequenced. In other words, even if the person has perfect privacy on his own genome, if the attacker has access to the DNA sequence of the relatives, he can obtain significant information about the person's DNA sequence.

Even though, at this stage, the field of genomics is generally free from serious attacks, it is likely that the above threats will become more serious as the number of sequenced individuals becomes larger. Such was the case of the Internet that was initially run and used by well-intentioned researchers. However, once it became more widely used, it became plagued by uncountable attacks such as spyware, viruses, spam, botnets, Denial-of-Service attacks, etc. Therefore, the need to adapt PETs to personal genomic data will only grow with time, as they are key tools for preventing an adversary from linking particular genomic data to a specific person or from inferring privacy-sensitive genomic data about a person.

It is obvious that users need to reveal personal and even privacy-sensitive information for genomic tests (e.g., paternity tests, disease-susceptibility tests, etc.). Nevertheless, they want to control how this information is used by the service providers (e.g., medical units such as healthcare centers or pharmaceutical companies, depending on the type of the test). Currently, the companies and hospitals that perform DNA sequencing store the genomic data of their customers and patients. Of course, tight legislation regulates their activities, but it is extremely difficult for them to protect themselves against the misdeeds of a hacker or a disgruntled employee. In a non-adversarial scenario, however, making use of this data requires legitimate professionals (e.g., physicians and pharmacists) to access the data in some way. Therefore, new architectures and protocols are needed to store and process this privacy-sensitive genomic data, while still enabling its utilization by the service providers (e.g., medical units).

In this work, our goal is to protect the privacy of users' genomic data while enabling medical units to access the genomic data in order to conduct medical tests or develop personalized medicine methods. In a medical test, a medical unit checks for different health risks (e.g., disease susceptibilities) of a user by using specific parts of his genome. Similarly, to provide personalized medicine, a pharmaceutical company tests the compatibility of a user on a particular medicine, or a pharmacist checks the compatibility of a given medicine (e.g., over-the-counter drug) to a given user. In both scenarios, in order to preserve his privacy, the user does not want to reveal his complete genome to the medical unit or to the pharmaceutical company. Moreover, in some scenarios, it is the pharmaceutical companies who do not want to reveal the genetic properties of their drugs. To achieve these goals, we propose to store the genomic data at a Storage and Processing Unit (SPU) and conduct the computations on genomic data utilizing homomorphic encryption and proxy encryption to preserve the privacy of the genomic data.

The rest of the paper is organized as follows. In the rest of this section, we discuss the challenges in genomic privacy and summarize the related work on genomic privacy. In Section 2, we describe our proposed schemes for privacy-preserving medical tests and personalized medicine. Furthermore, we analyze the level of privacy provided by the proposed schemes for different design and genomic criteria. Then, in Section 3, we discuss the implementation of the proposed schemes and present their complexity and security evaluations.

Finally, in Section 4, we conclude the paper and discuss new research directions on genomic privacy.

1.1 Challenges of Genomic Privacy

Obviously, there are certain obstacles for achieving our goals on genomic privacy. These are mostly due to (i) the balance between privacy and reliability of the genomic data, (ii) the structure of the human genome, and (iii) the evolution of the genomic research.

PETs generally protect users' privacy by either breaking the link between individuals' identities and the data they provide (e.g., removing user's identities from the published genomic data), or by decreasing the information provided (e.g., by using cryptographic tools or obfuscation techniques). Both techniques might reduce the reliability and the accuracy of the genomic data. Thus, a major issue to be addressed when designing PETs is limiting private information leakage while keeping an acceptable level of reliability and accuracy of the genomic data for the researchers and medical units.

Moreover, developing PETs for genomic data has many unique challenges, due to the architecture of the human genome. The human genome is encoded in double stranded DNA molecules consisting of two complementary polymer chains. Each chain consists of simple units called nucleotides (A,C,G,T). The human genome consists of approximately three billion letters. Existing privacy-preserving methods do not scale to these large genomic data sizes; hence current algorithms are inadequate for privacy protection on the genomic level.

Finally, the rapid evolution in the field of genomics produces many new discoveries every year, which cause significant changes in the known facts. For example, the sensitivity of certain genomic information will change over time; hence it is crucial to develop dynamic algorithms that can smoothly adapt to this rapid evolution.

1.2 Related Work

Due to the sensitivity of genomic data, research on the privacy of genomic data has considerably accelerated over the past few years. We can put the research on genomic privacy in three main categories: (i) private string searching and comparison, (ii) private release of aggregate data, and (iii) private clinical genomics.

In [6], Troncoso-Pastoriza et al. propose a protocol for string searching, which is then improved by Blanton and Aliasgari [7]. In this approach, one party with his own DNA snippet can verify the existence of a short template within his snippet by using a Finite State Machine in an oblivious manner. To compute the similarity of DNA sequences, in [8], Jha et al. propose techniques for privately computing the edit distance of two strings by using garbled circuits. In [9], Bruekers et al. propose privacy-enhanced comparison of DNA profiles for identity, paternity and ancestry tests using homomorphic encryption. Similar to our work, in [10], Kantarcioglu et al. propose using homomorphic encryption to perform scientific investigations on integrated genomic data. In their scheme, all genomic data is encrypted by the same public key of the data storage site, and there is a single key holder site which can decrypt everything. Thus, a curious party at the key holder site can obtain the genomic information of all users in case of a possible data leakage from the data storage site. Moreover, in [10], only the encrypted variants (i.e., positions in the genome holding a nucleotide that varies between individuals) of the users are stored at the data storage site along with their plaintext locations (on the DNA), which can leak substantial information to the data storage site about the genomic sequences of the users, as we discuss in Section 2.4. As opposed to [10], we focus on personal use of genomic data (e.g., in medical tests and personalized medicine methods), propose methods in which each user's genomic data is encrypted via his own cryptographic key, and prevent the leakage of genomic data due to statistical dependence between the variants. In one of the recent works [11], Baldi et al. make use of both medical and cryptographic tools for privacy-preserving paternity tests, personalized medicine, and genetic compatibility tests. Instead of utilizing public key encryption protocols, in [12], Canim et al. propose securing the biomedical data using cryptographic hardware. Finally, in [13], Eppstein et al. propose a privacy-enhanced method for comparing two compressed DNA sequences by using Invertible Bloom Filter [14].

When releasing databases consisting of aggregate genomic data (e.g., for research purposes), it is shown that known privacy-preserving approaches (e.g., de-identification) are ineffective on (un-encrypted) genomic data [15, 16]. Homer et al. [17] prove that the presence of an individual in a case group can be determined using aggregate allele frequencies and his DNA profile. In another recent study [18], Gitschier shows that a combination of information, from genealogical registries and a haplotype analysis of the Y chromosome collected for the HapMap project, allows for the prediction of the surnames of a number of individuals held in the HapMap database. Thus, releasing genomic data (even in aggregate form) is currently banned by many institutions due to this privacy risk. In [19], Zhou et al. study the privacy risks of releasing the aggregate genomic data. They propose a risk-scale system to classify aggregate data and a guide for the release of such data. Recently, using differential privacy was proposed by Fienberg et al. [20]; they aim to ensure that two aggregated databases, differing from each other by only one individual's data (e.g., DNA sequence), have indistinguishable statistical features.

Recently, in [21], utilizing a public cloud, Chen et al. propose a secure and efficient algorithm to align short DNA sequences to a reference (human) DNA sequence (i.e., read mapping). Finally, in [22], Wang et al. propose a privacy-protection framework for important classes of genomic computations (e.g., search for homologous genes), in which they partition a genomic computation, distributing sensitive data to the data provider and the public data to the data user.

In this work, we focus on medical tests (e.g., disease-susceptibility test) and personalized medicine methods by using users' genomic data while protecting user's genomic privacy. As a result of our extensive collaboration with geneticists, clinicians, and biologists, we conclude that DNA string comparison is insufficient in many medical tests (that use genomic data) and would not be enough to pave the way to personalized medicine. As it will become clearer in the next sections, specific variants must be considered individually for each genetic test. Thus, as opposed to the above private string search and comparison techniques, which focus on privately comparing the distance between the genomic sequences, we use the individual variants of the users to conduct genetic disease susceptibility tests and develop personalized medicine methods. We consider the individual contribution of each variant to a particular disease, for which a string comparison algorithm (such as Private Set Intersection [23, 24]) would not work. Further, in our proposed algorithms, we consider the statistical relationship between the variants for the genomic privacy of the users. In addition, we make use of a Storage and Processing Unit (SPU) between the user (patient) and the medical unit to store the genomic data in encrypted form and make computations on it using homomorphic encryption and proxy encryption.

1.3 Brief Description of the Invention

The aim of the present invention is to propose a privacy-enhancing method for medical tests and personalized medicine methods, which utilize patients' genomic data. It is proposed a method to process genomic data comprising the steps of:

at an initialization stage:
  associating a patient identification ID for a given patient P,
  generating a pair of asymmetric keys related to said patient P comprising a private and a public key,
  preparing a DNA sequence for said patient P comprising approved variants (such as SNPs or SVs), said approved variants being approved by medical authorities, each approved variant representing a position in the genome and a value representing a nucleotide that varies between individuals,
  extracting real and potential variants from said approved variants, said real and potential variants having each a position, said real variants being a subset of the approved variants and are different for each human being, said potential variants being the remaining part of the approved variants,
  encrypting the value of each real variant with the public key of the patient,
  storing the encrypted values with their respective positions into a Storage and Processing Unit (SPU), as well as the patient identification ID,
  dividing the private key into at least a first and a second part,
  transmitting the first part of the private key to the SPU, at a test stage:
  providing the second part of the private key to a medical unit MU,
  selecting by the medical unit MU a genetic test to be carried out and the related genetic markers, each marker having a position and a contribution,
  determining the contribution of each marker according to the genetic test selected,
  transmitting by the MU the genetic markers with their respective contribution to the SPU as well as an identification ID of the patient P,
  retrieving by the SPU the encrypted values for said patient P matching the position of the genetic markers, and for said patient,
  executing by the SPU a genetic test by using the retrieved values, and the contribution of those markers thanks to homomorphic operations,
  decrypting the result of the genetic test using the first part of the private key,
  sending the decrypted result to the MU,
  using the second part of the private key to obtain the final result.

The method of the invention is split into a first phase in which the DNA sequence is processed and stored in the SPU and a second phase during which a test is carried out.

During the first phase, the DNA sequence, produced by an authorized laboratory, is processed and encrypted as explained above. During this second phase, the medical test selected by the medical unit is carried out without having the possibility to retrieve all information of the patient.

The method proposed by the invention is based on the use of homomorphic encryption and proxy encryption. Assuming the whole genome sequencing is done by a certified institution, we propose to store patients' genomic data encrypted by their public keys at a Storage and Processing Unit (SPU). The proposed algorithm lets the SPU (or the medical unit) process the encrypted genomic data for medical tests and personalized medicine methods while preserving the privacy of patients' genomic data. We extensively analyze the relationship between the storage cost (of the genomic data), the level of genomic privacy (of the patient), and the characteristics of the genomic data. Furthermore, we implement and show via a complexity analysis the practicality of the proposed schemes. Finally, we evaluate the security of the proposed schemes and propose new research directions on genomic privacy.

1.4 Brief Description of the Figures

The invention will be better understood thanks to the attached figures in which:

The FIG. 1 illustrates the General architecture between the patient, SPU, and the medical unit.

Figure 2:
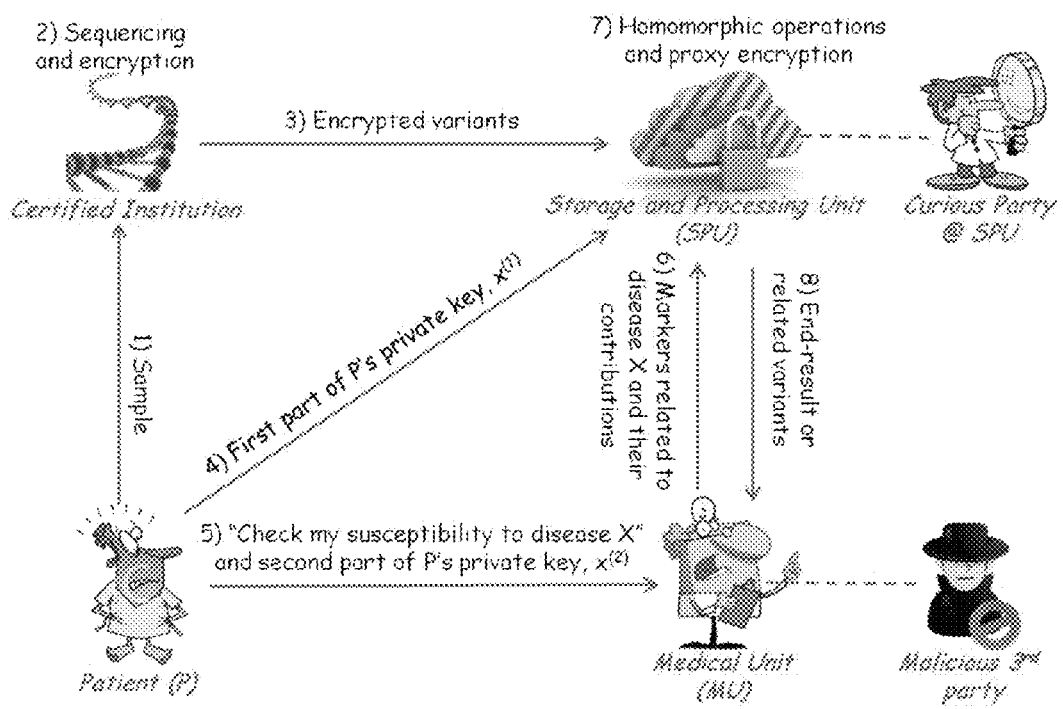

The FIG. 2 illustrates the Privacy-preserving protocol for disease-susceptibility test using Method 1 or Method 2.

Figure 3:
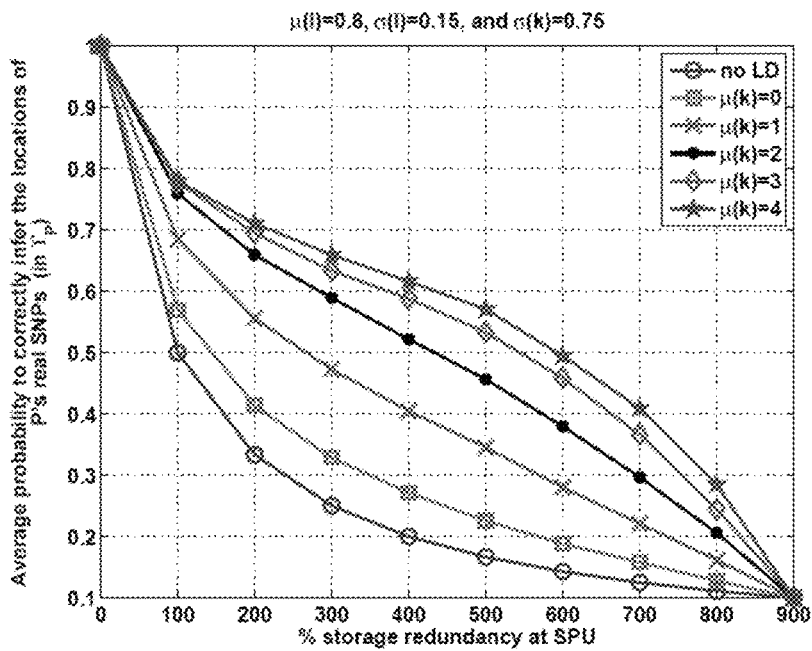

The FIG. 3 illustrates the Average probability to correctly infer the locations of patient's real SNPs (for the curious party at the SPU) with varying mean values of the number of LD pairs per SNP (i.e., $\mu(k)$) and storage redundancy.

Figure 4:
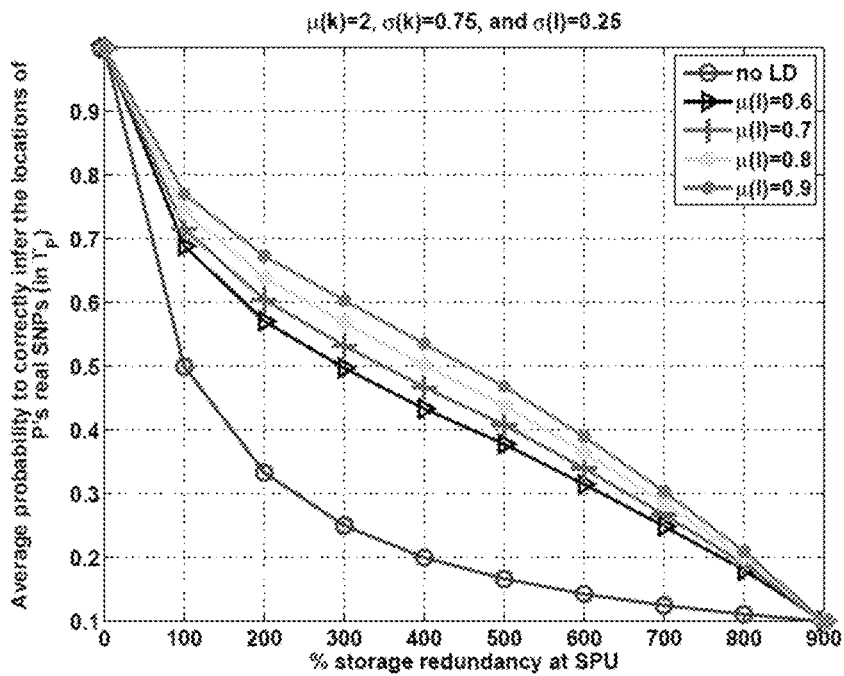

The FIG. 4 illustrates the Average probability to correctly infer the locations of patient's real SNPs (for the curious party at the SPU) with varying mean values of the LD strength between two SNPs (i.e., $\mu(l)$) and storage redundancy.

Figure 5:
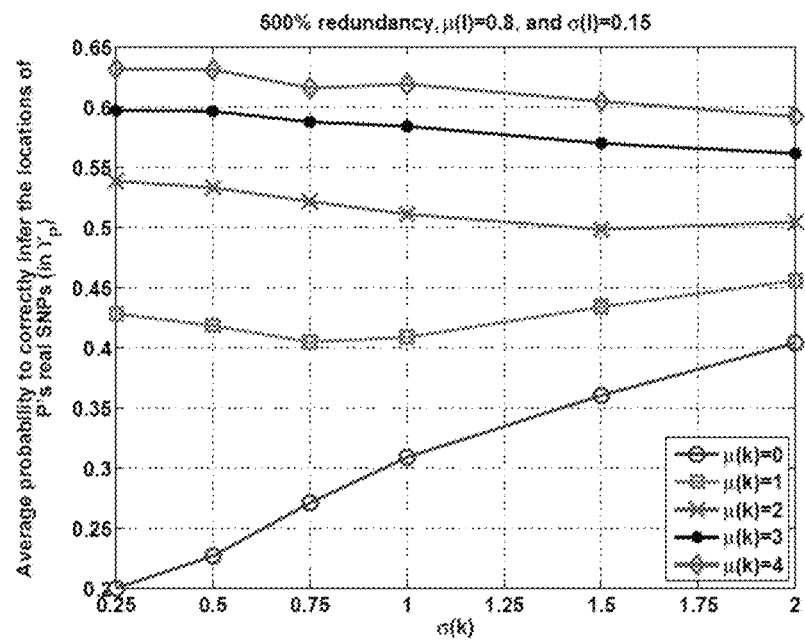

The FIG. 5 illustrates the Average probability to correctly infer the locations of patient's real SNPs (for the curious party at the SPU) with varying standard deviation and mean values of the number of LD pairs per SNP (i.e., $\sigma(k)$ and $\mu(k)$) and storage redundancy.

Figure 6:
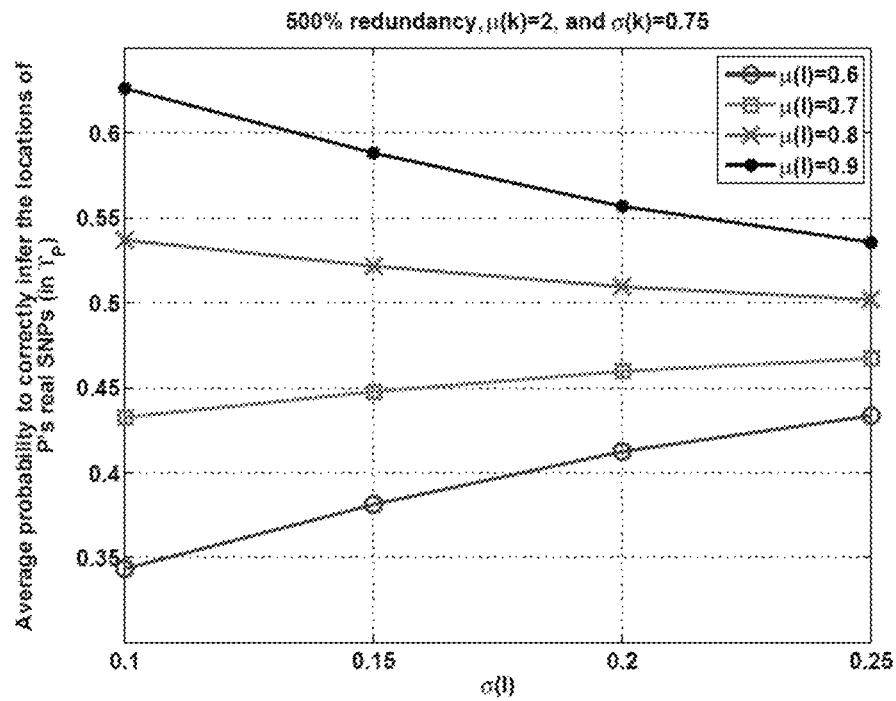

The FIG. 6 illustrates the Average probability to correctly infer the locations of patient's real SNPs (for the curious party at the SPU) with varying standard deviation and mean values of the LD strength between two SNPs (i.e., $\sigma(l)$ and $\mu(l)$) and storage redundancy.

Figure 7:
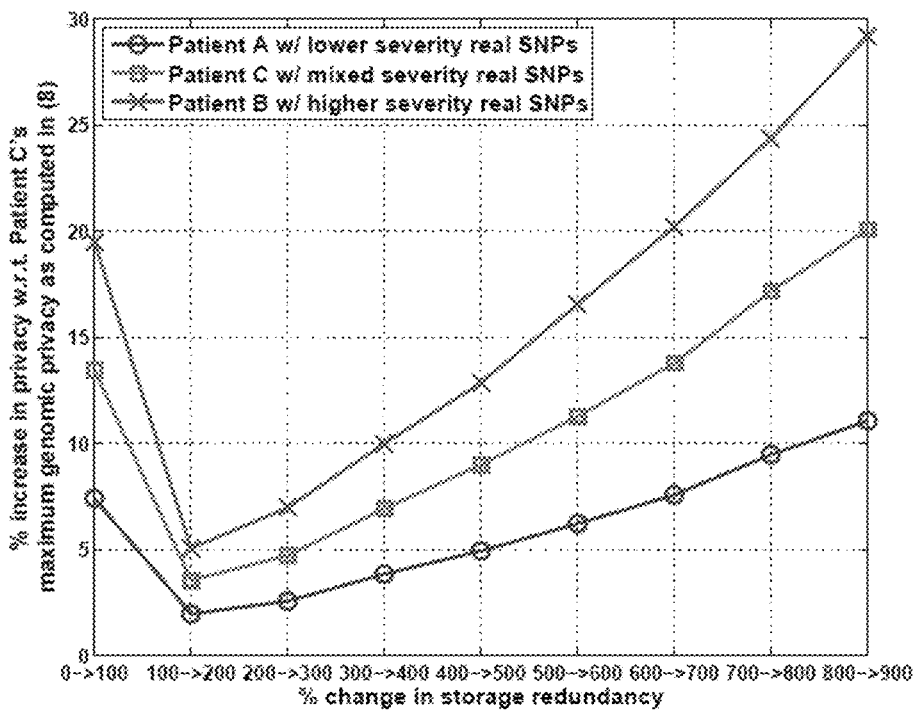

The FIG. 7 illustrates the Increase in genomic privacy of different types of patients with 100% increments in the storage redundancy. For example, increasing the storage redundancy from 400% to 500% would increase the privacy of Patient A (who carries mostly low severity real SNPs) by 5%, whereas the same scenario increases the privacy of Patient B (who carries mostly high severity SNPs) by 13%.

Figure 8:
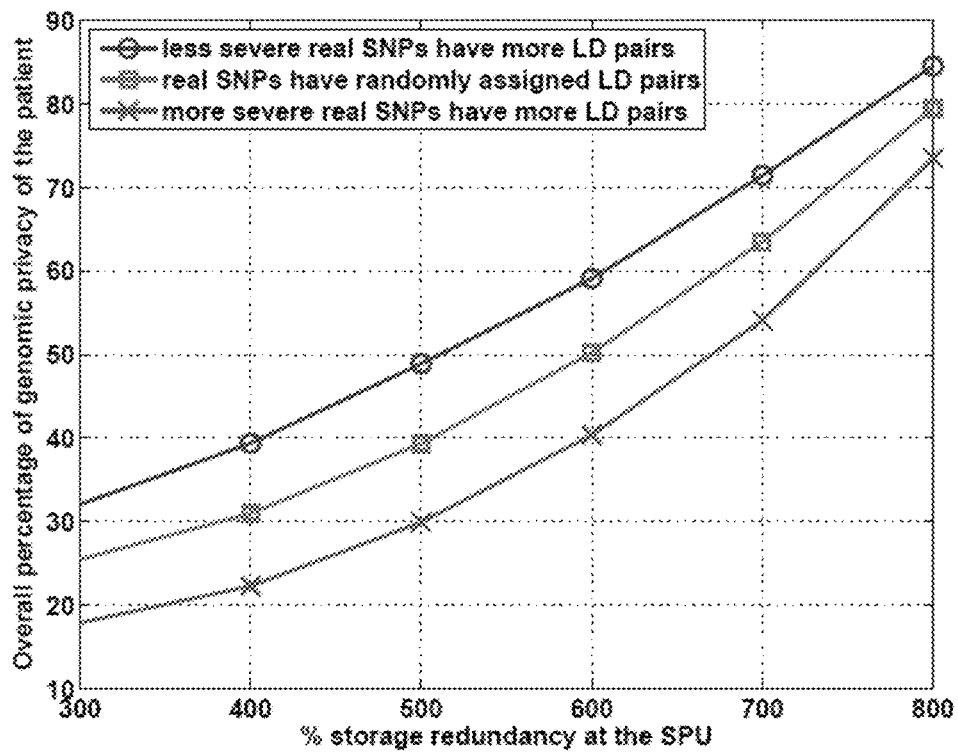

The FIG. 8 illustrates the Level of genomic privacy, as defined by (8), for different types of patients with varying storage redundancy.

Figure 9:
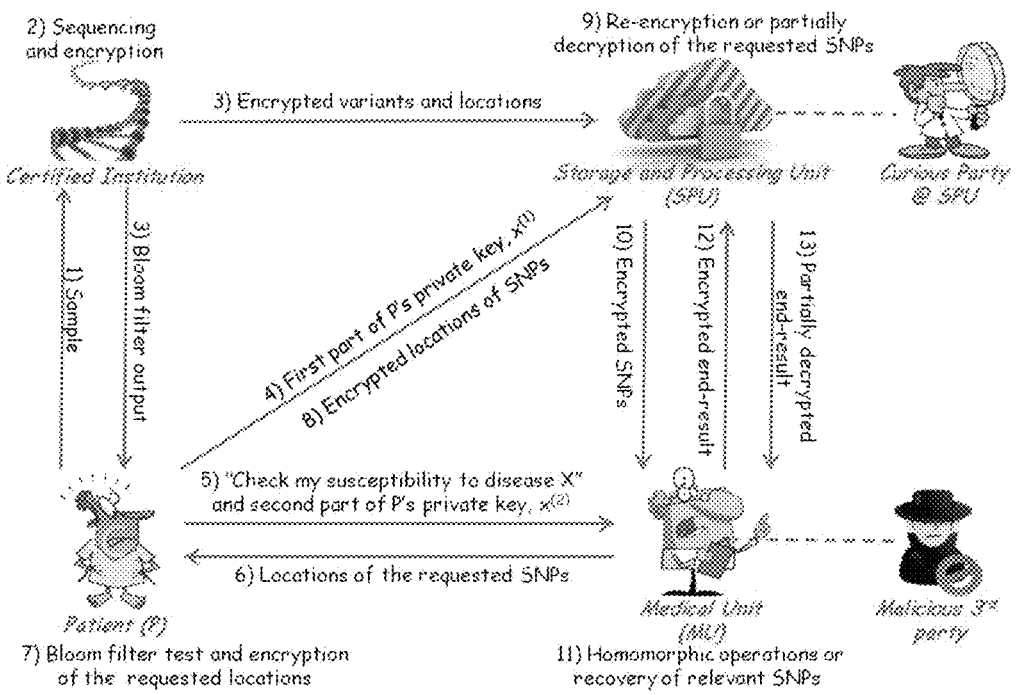

The FIG. 9 illustrates the Privacy-preserving protocol for disease-susceptibility test using Method 3.

Figure 10:
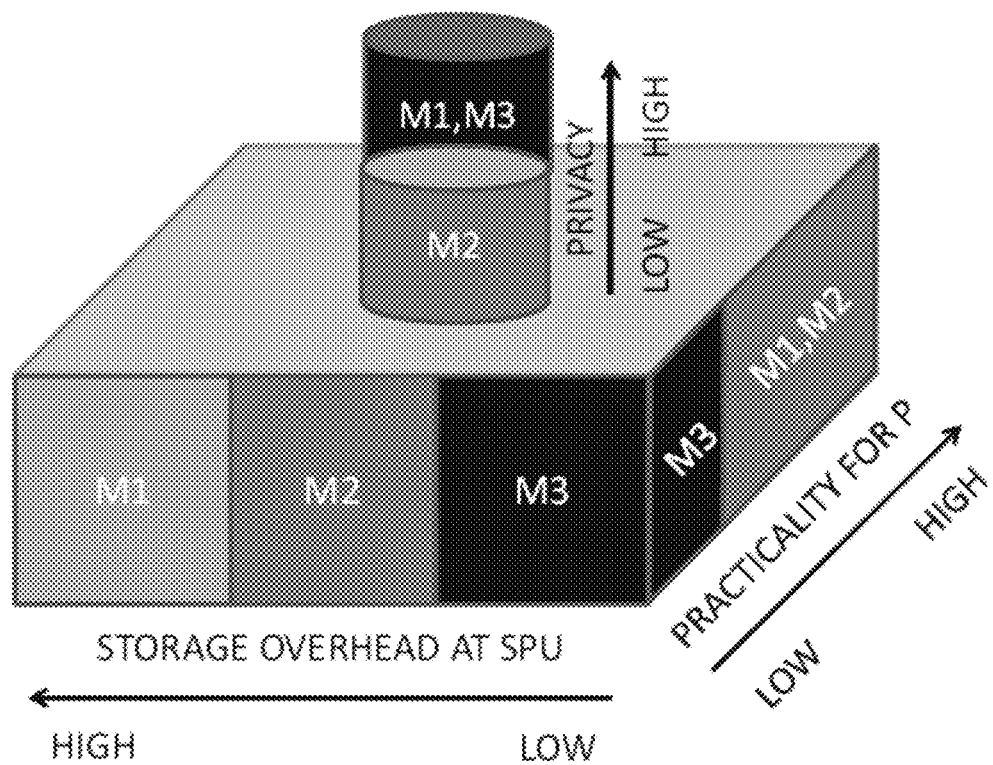

The FIG. 10 illustrates the Privacy, practicality, and storage overhead comparison of the proposed methods.

2 PETS FOR MEDICAL TESTS AND PERSONALIZED MEDICINE METHODS

In the present case, we study the privacy issues of medical tests and personalized medicine methods. Most medical tests and personalized medicine methods (that use genomic data) involve a patient and a medical unit. The patient is identified by a patient identification (ID), which could be a user name or a pseudonym (e.g., hash value of his social security number). In general, the medical unit is the family doctor, a physician, a pharmacist, or a medical council. In this study, we consider a malicious medical unit as the potential attacker. That is, a medical unit can be a malicious institution trying to obtain private information about a patient. Even if the medical unit is non-malicious, it is extremely difficult for medical units to protect themselves against the misdeeds of a hacker or a disgruntled employee. Similarly, the genomic data is too sensitive to be stored on users' personal devices (mostly due to security, availability, and storage issues), hence it is risky to leave the users' genomic data in their own hands. In addition, extreme precaution is needed between the patient and the medical unit due to the sensitivity of genomic data. Thus, we believe that a Storage and Processing Unit (SPU) should be used to store and process the genomic data. We note that a private company (e.g., cloud storage service), the government, or a non-profit organization could play the role of the SPU. We also assume that the SPU is an honest organization, but it might be curious (e.g., existence of a curious party at the SPU), hence genomic data should be stored at the SPU in encrypted form (i.e., the SPU should not be able to access the content of patients' genomic data). This general architecture is illustrated in FIG. 1.

For the simplicity of presentation, in the rest of this section, we will focus on a particular medical test (namely, computing genetic disease susceptibility). We note that similar techniques would apply for other medical tests and personalized medicine methods. In a typical disease-susceptibility test, a medical unit (MU) wants to check the susceptibility of a patient (P) to a particular disease X (i.e., probability that the patient P will develop disease X). It is shown that a genetic disease-susceptibility test can be realized by analyzing particular genetic variants of the patient via some operations, such as weighted averaging [25] or Likelihood Ratio (LR) test [26]. For simplicity, we focus on the simplest type of variant, the Single Nucleotide Polymorphism (SNP). Yet, the proposed methods are also valid for more complex types of variants such as the Structural Variants (SVs) that include among others: Copy-number Variations (CNVs), Inversions, Insertions, Deletions, etc. A SNP is a position in the genome holding a nucleotide (A, T, C or G), which varies between individuals. For example, it is reported that there are three particular genes bearing a total of ten particular SNPs necessary to analyze a patient's susceptibility to Alzheimer's disease [27]. Each SNP contributes to the susceptibility in a different amount and the contribution amount of each SNP is determined by previous studies on case and control groups (these studies are published in several papers). Furthermore, some of the SNPs contribute to the development of a disease, whereas some are protective.

In general, there are two alleles observed at a given SNP position: (i) The major allele is the most frequently observed nucleotide, and (ii) the minor allele is the rare nucleotide. Everyone inherits one allele of every SNP location from each of his parents. If an individual receives the same allele from both parents, he is said to have a homozygous variant for that SNP location. If, however, he inherits a different allele from each parent (one minor and one major), he has a heterozygous variant. There are approximately 40 million approved variants (SNPs) in the human population as of now (according to the NCBI dbSNP [28]) and each patient carries on average 4 million SNPs (i.e., real variants) out of this 40 million. Moreover, this set of 4 million SNPs is different for each patient. From now on, to avoid confusion, for each patient, we refer to these 4 million variants as the real SNPs and the remaining non-variants (approved SNPs that do not exist for the considered patient) as the potential SNPs of the patient; when we only say "SNPs", we mean both the real and potential SNPs.

At this point, it can be argued that these 4 million real SNPs (nucleotides) could be easily stored on the patient's computer or mobile device, instead of the SPU. However, we assert that this should be avoided due to the following issues. On one hand, the number of approved SNPs in human population continues to increase with new discoveries. Further, as mentioned above, types of variations in human population are not limited to SNPs, and there are other types of variations such as Copy-Number Variations (CNVs), rearrangements, or translocations (our proposed privacy-preserving mechanisms can be smoothly adapted for these alternative variations), consequently the required storage per patient is likely to be considerably more than only 4 million nucleotides. This higher storage cost might still be affordable to an average patient (via desktop computers or USB drives), however, genomic data of the patient should be available any time (e.g., for emergencies), thus it should be stored at a reliable source such as the SPU. On the other hand, as we discussed before, leaving the patient's genomic data in his own hands and letting him store it on his computer or mobile device is risky, because his mobile device can be stolen or his computer can be hacked.

A potential attacker can learn about the susceptibilities of the patient to privacy-sensitive diseases if he obtains some specific real SNPs of the patient. Moreover, the knowledge of 75 real SNPs (out of approximately 4 million), if not fewer, will enable the attacker to identify a person [29]. These situations could lead to genetic discrimination such as denying a person's access to health (or life) insurance or obstructing his employment opportunities. As we discussed before, in our setting, both the MU and SPU pose a threat to the patient's privacy. On one hand, the MU can either be a malicious institution trying to obtain private information about the patient or it can be hacked by another malicious entity. On the other hand, the SPU is considered as an honest but curious entity. Thus, our goal is to build mechanisms in which the patient can preserve the privacy of his genomic sequence (his real genetic variants) while enabling the MU to access his genomic data and conduct genetic tests.

We assume that the whole genome sequencing is done by a Certified Institution (CI) with the consent of the patient. Moreover, the genomic data of the patient is encrypted by the same CI (using the patient's public key) and uploaded to the SPU so that only the patient can decrypt the stored (potential or real) SNPs, and the SPU cannot access the SNPs of the patient. We are aware that the number of discovered SNPs increases with time. Thus, the patient's complete DNA sequence is also encrypted as a single vector file (via symmetric encryption using the patient's key) and stored at the SPU, thus when new SNPs are discovered, these can be included in the pool of the previously stored SNPs of the patient. We also assume the SPU does not have access to the real identities of the patients and data is stored at the SPU by using pseudonyms; this way, the SPU cannot associate the conducted genomic tests to the real identities of the patients. As an alternative, the privacy of the genomic data at the SPU can be further increased using privacy enhanced access control [30] or Oblivious RAM (O-RAM) storage [31] techniques, in which the data access patterns are completely hidden from the server (SPU). Note that even the most efficient implementation of O-RAM introduces high storage overhead to the client (patient), and it introduces 20~25 times more overhead with respect to non-oblivious storage. Thus once it becomes more efficient, O-RAM storage could be considered as a future add-on to the proposed privacy-preserving mechanisms.

Depending on the access rights of the MU, the SPU can either (i) compute Pr(X), the probability that the patient will develop the disease X by checking the patient's encrypted variants via homomorphic encryption techniques [33] (In one of our proposed schemes, see Method 3 in Section 2.4, Pr(X) is computed at the MC via homomorphic operations), or (ii) provide the relevant variants to the MU (e.g., for complex diseases that cannot be interpreted using homomorphic operations). These access rights are defined either jointly by the MU and the patient or by the medical authorities. Further, access rights can be enforced by using a secure attribute-based system as in [34]. We note that homomorphic encryption lets the SPU (or MU) compute Pr(X) using encrypted variants of the patient P. In other words, the SPU (or MU) does not access P's variants to compute his predicted disease susceptibility. We use a modification of the Paillier cryptosystem (described in Section 2.1) to support the homomorphic operations at the SPU (or MU).

We propose four different techniques for the storage and process of the SNPs at the SPU and the preservation of the patient's privacy: (i) Method 0 in Section 2.2, (ii) Method 1 in Section 2.3, (iii) Method 2 in Section 2.4, and (vi) Method 3 in Section 2.5. We describe these proposed techniques in detail in the following subsections. We also discuss the computation of genetic disease susceptibility by using homomorphic operations in Section 2.6.

In the rest of this work, for simplicity of the presentation, we do not consider the type of the variant at a real SNP location (i.e., whether the variation is homozygous or heterozygous for that real SNP); we only consider whether the patient has a real SNP or not at a particular location. However, the proposed approaches and the analysis (in Section 2.4) can easily be extended to cover the types of the variants. In order to facilitate future references, frequently used notations are listed in Table I for the different stages of the proposed schemes.

TABLE I

NOTATIONS AND DEFINITIONS.

| General Notations | |
|---|---|
| $SNP_i^P$ | Type of SNP i, $SNP_i$, of the patient P. $SNP_i^P \in \{0, 1\}$, 0 representing a potential SNP (i.e., non-variant) for P, and 1 representing a real SNP (i.e., a variant) for P. |
| $S_P^X$ | Predicted susceptibility of the patient P to disease X. |
| $\gamma_P$ | Set of real SNPs of the patient P (SNPs at which P has a variant: around 4 million at each patient). |
| $\Omega_P$ | Set of potential SNPs of the patient P (SNPs at which P does not have a variant: around 36 million at each patient). |
| Cryptographic Notations | |
| n, g | Public parameters of modified Paillier cryptosystem. |
| x | Weak private key of the patient P. |
| $x^{(i)}$ | $i^{th}$ share of the patient P's private key. |
| $g^x$ | Public key of the patient P. |
| $E(m, g^x)$ | Encryption of message m with the patient P's public key. |
| Susceptibility Test via Weighted Averaging | |
| $p_j^i(X)$ | Probability that P would develop disease X, given $SNP_i^P = j$, $Pr(X|SNP_i^P = j)$. |
| $C_i^X$ | Contribution of $SNP_i$ to the susceptibility to disease X. |
| Susceptibility Test via Likelihood Ratios | |
| $I_X^P$ | Initial risk of the patient P for disease X. |
| $L_X^i(j)$ | Likelihood Ratio (LR) when $SNP_i = j$ for disease X. |

2.1 Paillier Cryptosystem

In this section, we briefly review the modified Paillier cryptosystem (described in detail in [33, 35]), which we use in this work, and its homomorphic properties. We note that the usual notation in Paillier cryptosystem is to use a pair of keys named public and secret key. However, for the present description, we will use the denote the keys as public and private.

The public key of the patient P is represented as (n, g, $h=g^x$), where the strong private key is the factorization of n=pq (p, q are safe primes), the weak private key is $x\in[1, n^2/2]$, and g of order (p−1)(q−1)/2. Such a g can be easily found by selecting a random $a\in Z^*_{n^2}$, and computing $g=a^{2n}$.

Encryption of a Message: To encrypt a message $m\in Z^*_{n^2}$, we first select a random $r\in[1, n/4]$ and generate the ciphertext pair $(T_1, T_2)$ as below:

$$T_1 = g^r \bmod n^2 \text{ and } T_2 = h^r(1+mn) \bmod n^2. \quad (1)$$

Re-Encryption of a Message:
An encrypted message $(T_1, T_2)$ can be re-encrypted under the same public key, using a new random number $r_1\in[1, n/4]$ as below:

$$\hat{T}_1 = g^{r_1}T_1 \bmod n^2 \text{ and } \hat{T}_2 = h^{r_1}T_2 \bmod n^2. \quad (2)$$

Decryption of a Message: The message m can be recovered as follows:

$$m = \Lambda(T_2/T_1^x), \quad (3)$$

where $\Lambda(u) = \dfrac{(u-1) \bmod n^2}{n}$, for $u \in \{u < n^2 \mid u \equiv 1 \bmod n\}$.

Homomorphic Properties:

Assume two messages $m_1$ and $m_2$ are encrypted using two different random numbers $r_1$ and $r_2$, under the same public key, $(n, g, h=g^x)$, such that $E(m_1, r_1, g^x)=(T_1^1, T_2^1)$ and $E(m_2, r_2, g^x)=(T_1^2, T_2^2)$. Assume also that c is a constant number. Then the below-mentioned homomorphic properties are supported by Paillier cryptosystem:

The product of two ciphertexts will decrypt to the sum of their corresponding plaintexts.

$$D(E(m_1,r_1,g^x) \cdot E(m_2,r_2,g^x))=D(T_1^1 \cdot T_1^2 \cdot T_2^1 \cdot T_2^2 \bmod n^2)=m_1+m_2 \bmod n. \quad (4)$$

An encrypted plaintext raised to a constant c will decrypt to the product of the plaintext and the constant.

$$D(E(m_1,r_1,g^x)^c)=D((T_1^1)^c,(T_2^1)^c \bmod n^2)=cm_1 \bmod n. \quad (5)$$

These homomorphic operations are conducted at the SPU (or MU depending on which approach is used) to compute the predicted susceptibility of the patient P to disease X, as will be discussed in Section 2.6.

Proxy encryption: The patient's weak private key x is divided (preferably randomly or by any other rule) into two shares: $x^{(1)}$ and $x^{(2)}$ (such that $x=x^{(1)}+x^{(2)}$). $x^{(1)}$ is given to the SPU and $x^{(2)}$ is given to the MU. Using the above Paillier cryptosystem, an encrypted message $(T_1, T_2)$ (under the patient's public key) can be partially decrypted by the SPU (using $x^{(1)}$) to generate the ciphertext pair $(\tilde{T}_1, \tilde{T}_2)$ as below:

$$\tilde{T}_1=T_1 \text{ and } \tilde{T}_2=T_2/T_1^{x^{(1)}} \bmod n^2. \quad (6)$$

Now, $(\tilde{T}_1,\tilde{T}_2)$ can be decrypted at the MU using $x^{(2)}$ to recover the original message. $x^{(2)}$ can be provided to the MU once the patient is registered to the medical unit or through the patient's digital ID card. Further details about the distribution of shares are out of the scope of this paper. We note that this approach is not proxy re-encryption; it is based on secret-sharing.

Overall, this modified Paillier cryptosystem is not key optimal, because the size of the MU's and SPU's secret storages do not remain constant. That is, both the MU and SPU need to store a secret for every patient.

However, this storage cost can be considered negligible when compared to the storage of the genomic data. Further, the shares (e.g., $x^{(1)}$ and $x^{(2)}$) can be stored by the patient and sent to the MU and SPU only when it is needed in order to resolve this storage issue at the expense of extra communication overhead. Furthermore, the above modified Paillier cryptosystem is not proxy invisible, because all participants of the systems (i.e., P, MU and SPU) should be aware of the existence of the proxy. We discuss the security evaluation of this cryptosystem in Section 3.2.

2.2 Method 0

Only Store the Real SNPS at the SPU

In this approach, the real SNPs of the patient are stored encrypted (via the patient's public key) and the locations of the corresponding real SNPs are stored in plaintext at the SPU.

We assume that $SNP_i$ at the patient P is represented as $SNP_i^P$ and $SNP_i^P=1$, if P has a real SNP (i.e., variant) at this location, and $SNP_i^P=0$, if P does not have a variant at this location. We let $Y_P$ be the set of real SNPs of the patient P (at which $SNP_i^P=1$). We also let P represent the set of potential SNPs (at which $SNP_i^P=0$).

Below, we summarize the proposed approach for the privacy protecting disease-susceptibility test by using this particular storage technique.

Step 0: The asymmetric keys (public and private keys) of each patient are generated and distributed to the patients during the initialization period. Then, symmetric keys are established between the parties, using which the communication between the parties is protected from an eavesdropper. We note that the distribution, update and revocation of cryptographic keys are handled by a trusted entity (similar to e-banking platforms).

Step 1: The patient (P) provides his sample (e.g., his saliva) to the Certified Institution (CI) for sequencing.

Step 2: The CI sequences P, and encrypts the contents of his real SNP locations (in $Y_P$) by using P's public key.

Step 3: The CI sends the encrypted real SNPs of P to the SPU (so that the SPU cannot access to P's SNPs).

Step 4: We divide the private key into a first and a second part, the patient provides the first part of his private key ($x^{(1)}$) to the SPU.

Step 5: The MU wants to conduct a susceptibility test on P to a particular disease X, and P provides the second part of his private key ($x^{(2)}$) to the MU as well as his identification ID.

Step 6: The MU provides genetic variant markers, along with their individual contributions (to the disease susceptibility), to the SPU.

Step 7: If the disease susceptibility can be interpreted by homomorphic operations, the SPU computes P's total susceptibility to disease X from the individual effects of SNPs by using the homomorphic properties of the Paillier cryptosystem as described in Section 2.6. Otherwise, the SPU provides the relevant real SNPs to the MU based on MU's access rights.

Step 7: The SPU partially decrypts the end-result (or the relevant SNPs) using the first part of P's private key for example by following a proxy encryption protocol (Section 2.1).

Step 8: The SPU sends the partially decrypted end-result (or the relevant real SNPs) to the MU.

Step 9: The MU decrypts the message received from the SPU using the second part of P's private key and recovers the end-result (or the relevant real SNPs).

2.3 Method 1

Plaintext Locations at the SPU

Method 0 in Section 2.2 might leak private information to the curious party at the SPU. As the locations of the SNPs are stored in plaintext, if the SPU only stores the real SNPs in $Y_P$, a curious party at the SPU can learn all real SNP locations of the patient, and hence, much about his genomic sequence. The nucleotides corresponding to variants at particular locations of the DNA sequence are public knowledge. Thus, even though the contents of patient's real SNPs are encrypted, a curious party at the SPU can infer the nucleotides corresponding to these SNPs from their plaintext locations. Therefore, in this method, the SPU stores the contents of both real and potential SNP locations (in $\{Y_P \cup \Omega_P\}$) in order to preserve the privacy of the patient. The locations of the corresponding SNPs are again stored in plaintext at the SPU. This is because, when a particular SNP (or set of SNPs) are queried by the MU, the SPU should know which SNPs to process (or send to the MU).

As before, we assume that $SNP_i$, at the patient P is represented as $SNP_i^P$ and $SNP_i^P=1$, if P has a real SNP (i.e., variant) at this location, and $SNP_i^P=0$, if P does not have a variant at this location. We let $Y_P$ be the set of real SNPs of the patient P (at which $SNP_i^P=1$). We also let P represent the set of potential SNPs (at which $SNP_i^P=0$). Below, we summarize the proposed approach for the privacy protecting disease-susceptibility test by using this particular storage technique. This approach is illustrated in FIG. 2.

Step 0: The asymmetric keys (public and private keys) of each patient are generated and distributed to the patients during the initialization period. Then, symmetric keys are established between the parties, using which the communication between the parties is protected from an eavesdropper. We note that the distribution, update and revocation of cryptographic keys are handled by a trusted entity (similar to e-banking platforms).

Step 1: The patient (P) provides his sample (e.g., his saliva) to the Certified Institution (CI) for sequencing.

Step 2: The CI sequences P, and encrypts the contents of his real and potential SNP locations (in $\{Y_P \cup \Omega_P\}$) by using P's public key.

Step 3: The CI sends the encrypted SNPs of P to the SPU (so that the SPU cannot access to P's SNPs).

Step 4: We divide the private key into a first and a second part, the patient provides the first part of his private key ($x^{(1)}$) to the SPU.

Step 5: The MU wants to conduct a susceptibility test on P to a particular disease X, and P provides the second part of his private key ($x^{(2)}$) to the MU as well as his identification ID.

Step 6: The MU provides genetic variant markers, along with their individual contributions (to the disease susceptibility), to the SPU.

Step 7: If the disease susceptibility can be interpreted by homomorphic operations, the SPU computes P's total susceptibility to disease X from the individual effects of SNPs by using the homomorphic properties of the Paillier cryptosystem as described in Section 2.6. Otherwise, the SPU provides the relevant SNPs to the MU based on MU's access rights.

Step 7: The SPU partially decrypts the end-result (or the relevant SNPs) using the first part of P's private key for example by following a proxy encryption protocol (Section 2.1).

Step 8: The SPU sends the partially decrypted end-result (or the relevant SNPs) to the MU.

Step 9: The MU decrypts the message received from the SPU using the second part of P's private key and recovers the end-result (or the relevant SNPs).

The above technique provides a high level of privacy and practicality for the patient, because (i) from the view point of a curious party at the SPU, inferring the locations of the patient's real SNPs with the stored information is equivalent to inferring them with no information about the patient, and (ii) the patient is not involved in the protocol after the sequencing (except for the consent between the patient and the MU for a particular test). However, this level of privacy and practicality comes at the cost of extra storage overhead at the SPU (due to the storage of both real and potential SNPs as discussed in Section 3.1).

2.4 Method 2

Redundant Storage at the SPU

Due to the significant storage overhead mentioned in Section 2.3, here we propose another technique that reduces the storage overhead at the SPU at the expense of decrease in privacy. In a nutshell, we leave everything the same as in Section 2.3, but, instead of storing the contents of all potential and real SNP locations, we store the real SNPs of the patient along with a certain level of redundancy (i.e., contents of some potential SNP locations). In other words, to mislead a curious party at the SPU, among the 40 million discovered SNPs, we store the approximately 4 million real SNPs (for which $SNP_i^P=1$, $i \in Y_P$) along with some redundant content from $\Omega_p$ (with $SNP_j^P=0$), for each patient.

Again, we assume that the location of the encrypted (real or potential) SNPs are stored in plaintext at the SPU and there exists a potential curious party at the SPU trying to infer the real SNPs of the patient (in $Y_P$). An important issue to consider in this approach is the Linkage Disequilibrium (LD) between SNPs [36].

LD occurs when SNPs at two loci (SNP positions) are not independent of each other. For simplicity, we represent the LD relationship between two SNPs i and j as $Pr(SNP_i|SNP_j)$, where $SNP_i$ (or $SNP_j$) takes values from the set $\{0, 1\}$. In compliance with genetic observations, we assume that the LD between two SNPs are not symmetric, i.e., $Pr(SNP_i|SNP_j) \neq Pr(SNP_j|SNP_i)$. We note that LD relationships are defined among all 40 million discovered SNPs, regardless of their type (i.e., real or potential) at a particular patient.

As in Section 2.3, the SPU provides the end-result of a disease-susceptibility test or the relevant SNPs to the MU. However, in this case, if a particular potential SNP (requested by the MU or needed in the susceptibility test) is not stored at the SPU (i.e., $SNP_j^P=0$), one of the following two scenarios occurs: (i) If the SPU provides the relevant SNPs to the MU, MU infers the missing potential SNPs from the reference genome (since it is known that the missing potential SNPs are not a variant for P), or (ii) if the SPU provides the end-result of the susceptibility test, the SPU uses the fact that $SNP_j^P=0$ for each missing potential $SNP_j$.

As expected, the amount of storage redundancy (due to the storage of the content from $\Omega_p$), along with the LD between the SNPs and their characteristics, determine the level of a patient's genomic privacy.

Therefore, in the rest of this section, we analyze the relationship between the amount of redundancy, LD values, characteristics of the SNPs, and the level of privacy. To do so, first, we observe the average probability of correctly inferring the locations of P's real SNPs (in $y_p$) considering varying amounts of redundancy and the LD values between the SNPs. That is, how much information from a patient's un-stored potential SNPs is revealed to the curious party at the SPU about the locations of his real SNPs? This problem can also be formulated similarly if the goal of the attacker is to determine the type of the variant at a real SNP location (e.g., homozygous or heterozygous). In this case, $SNP_i^P$ can take three different values from the set $\{0, 1, 2\}$, 0 representing a potential SNP (i.e., non-variant) 1 representing a real homozygous SNP, and 2 representing a real heterozygous SNP for P. It is worth noting that for this study, we create realistic models for the LD values and the characteristics of the SNPs. Further, for the created models, we try a wide range of parameters and observe a wide range of results to address most potential scenarios. However, as the field of genomics becomes more mature, our models can be replaced by the values obtained from the medical research.

We let $\Omega_p^s$ and $\Omega_p^u$ denote the set of P's potential SNPs that are stored (for redundancy) and not stored at the SPU, respectively ($\Omega_p^s \cup \Omega_p^u = \Omega_p$). Further, $K_i$ is the set of SNPs with which a particular SNP i has LD, and $|K_i|=k$ (for each SNP, these k SNPs are chosen among approximately 40 million SNPs). We assume that $k \geq 0$ and it is a truncated Gaussian random variable with only discrete values and obtained from a distribution with mean σ(k) and standard deviation (k).

Initially, we compute $Pr(SNP_i^P)$ for all (real and potential) SNPs in $\{Y_p \cup \Omega_p^z\}$ by using the LD relationships between these SNPs and those in $\Omega_p^u$. As all SNPs in $\{Y_p \cup \Omega_p^z\}$ are encrypted and stored at the SPU, only the LD relationships between these SNPs and the un-stored SNPs in $\Omega_p^u$ are helpful for the curious party.

Therefore, for each real SNP $i \in Y_p$, we observe $Pr(SNP_i^P=1|SNP_m^P=0)$ for all $m \in \{K_i(i) \cap \Omega_{lp}^{\prime} s\}-|\}$, get the average of these values, and compute $Pr(SNP_i^P=1)$. Similarly, for each potential SNP $j \in \Omega_p^s$, we observe $Pr(SNP_j^P=0|SNP_m^P=0)$ for all $m \in \{K_j \cap [\Omega_p^u)]$, average these values, and compute $Pr(SNP_j^P=0)$. We let $l$ be the indicator of the LD strength between two SNPs. Thus, we represent $Pr(SNP_i^P=1|SNP_m^P=0)=/(i \in Y_p, m \in \{K_i \cap [\Omega_p^u)])$ and $Pr(SNP_j^P=0|SNP_m^P=0)=/(j \in \Omega_{lp}^{\prime} s, m \in [K_i(j) \cap \Omega_{lp}^l u])$ as truncated Gaussian random variables with range [0.5, 1], obtained from a distribution with mean μ(l) and standard deviation σ(l).

Finally, if $|K_i|=k=0$ or $|K_j \cap \Omega_p^u|=0$ for a SNP i in $\{Y_p \cup \Omega_p^s\}$, we update $Pr(SNP_i^P=1)$ considering the fact that the expected value of all stored SNPs is known by the curious party as below:

$$\frac{1}{|Y_P \cup \Omega_P^s|} \sum_{j \in Y_P \Omega_P^s} (SNP_j^P) \times Pr(SNP_j^P) = \frac{|Y_P|}{|Y_P \cup \Omega_P^s|}. \quad (7)$$

In the following, we illustrate our numerical results that represent the relationship between storage, inference power of the curious party at the SPU, and LD values. We assume $|Y_P|=4$ million and $|Y_P \cup \Omega_P|=40$ million. We define the percentage of storage redundancy at the SPU as $$\frac{|\Omega_Z^S|}{|Y_P|}|_{\times 100}$$

and compute the average value of $Pr(SNP_i^P=1)$ for a SNP in $Y_P$ for varying values of μ(k), (k), μ(l), and σ(l). Higher values of $Pr(SNP_i^P=1)$ indicate a higher inference power for the curious party at the SPU. We repeat each simulation 100 times to obtain an average. Note that Method 1 (in Section 2.3) is a special case of Method 2 (when the storage redundancy at the SPU is 900%), hence its privacy is the same as 900% redundancy in the following results.

In FIG. 3, we illustrate the variance in the average value of $Pr(SNP_i^P=1)$ for different values of μ(k), when μ(l)=0.8, σ(l)=0.15, and σ(k)=0.75. We note that "no LD" curve in the figure represents the case in which the LD values between the SNPs are ignored. We observe that as the available side information (i.e., number of un-stored potential SNPs in $\Omega_p^u$ having LD with the stored ones) increases, the inference power of the curious party increases, especially for low values of storage redundancy. For example, to have the same inference power for the curious party, 200% storage redundancy is required when μ(k)=0, whereas it is 700% when μ(k)=4. Furthermore, even at the maximum (i.e, 900%) storage redundancy, the curious party still has a slight probability of inferring the variants of the patient, because it knows that 4 out of 40 million of the stored content are variants. Next, in FIG. 4, we illustrate the variance in the same probability, this time for different values of μ(l), when μ(k)=2, σ(k)=0.75, and σ(l)=0.25. For higher values of σ(l), the gap between the different μ(l) curves becomes negligible, because the distribution becomes almost uniform, rather than truncated Gaussian. As expected, the inference power of the curious party increases when the strength of LD between the SNPs increases (i.e., when μ(l) increases).

We observe that the strength of LD, however, does not affect the inference power as strong as k. Then, FIG. 3 illustrates the average probability to correctly infer the locations of patient's real SNPs (for the curious party at the SPU) with varying mean values of the number of LD pairs per SNP (i.e., μ(k)) and storage redundancy.

The FIG. 4 illustrates the average probability to correctly infer the locations of patient's real SNPs (for the curious party at the SPU) with varying mean values of the LD strength between two SNPs (i.e., μ(l)) and storage redundancy.

In the FIGS. 5 and 6, we show the Average$\{Pr(SNP_i^P=1)\}$ for varying standard deviations of k and l, and with 500% storage redundancy as follows: (i) in FIG. 5, we vary σ(k) and μ(k), when μ(l)=0.8 and σ(l)=0.15, and (ii) in FIG. 6, we vary σ(l) and μ(l), when μ(k)=2 and σ(k)=0.75. We observe that the inference power of the curious party varies (either increases or decreases) with an increasing value of σ(k) (σ(l)) depending on μ(k) (μ(l)), and, as expected, all curves converge to a single value for higher values of σ(k) (σ(l)).

Next, considering the individual characteristics of the real SNPs (i.e., their severity levels), we analyze the level of genomic privacy of a patient against a curious party at the SPU. By the level of genomic privacy, we understand the level of information that a third party can infer about the real variants of a patient. The severity of a SNP i can be defined as the privacy-sensitivity of the SNP when $SNP_i^P=1$ (i.e., when it exists as a variant at the patient P). For example, a real SNP revealing the predisposition of a patient for Alzheimer's disease can be considered more severe than another real SNP revealing his predisposition to a more benign disease. Severity values of the SNPs are determined as a result of medical studies (depending on their contributions to various diseases) and tables of disease severities provided by insurance companies (e.g., percentage of invalidity). We denote the severity of a real SNP i as Vi, and 0≤Vi≤1 (1 denotes the highest severity). Thus, we define the genomic privacy of the patient P as below:

$$\Phi_P = -\sum_{i \in \Upsilon_P} \log_2(Pr(SNP_i^P = 1)) \times V_i. \quad (8)$$

We do not use the traditional entropy metric [37, 38] to quantify privacy, as only one state of $SNP_i^P$ poses privacy risks (i.e. $SNP_i^P=1$), as discussed before.

First, we study the relationship between the storage redundancy and the severity of the real SNPs by focusing on three types of patients: (i) patient A, carrying mostly low severity real SNPs (in $Y_A$), (ii) patient B, carrying mostly high severity real SNPs (in $Y_B$), and (iii) patient C, carrying mixed severity real SNPs (in $Y_C$). For each patient, the highest level of privacy is achieved when the storage redundancy is maximum (as in Method 1 in Section 2.3). Thus, we recognize this level as 100% genomic privacy for the patient. For the evaluation, we take the highest privacy level of patient C as the base and normalize everything with respect to this value. We use the following parameters for the simulation. The severities of patient A's and patient B's real SNPs are represented as truncated Gaussian random variables with (μA, σA)=(0.25, 0.15) and (μB, σB)=(0.75, 0.15), respectively. Furthermore, the severity of patient C's real SNPs are represented as a uniform distribution between 0 and 1. We also set μ(l)=0.8, σ(l)=0.25, μ(k)=2, and σ(k)=0.75. In FIG. 7, we illustrate the increase in privacy with increments in the storage redundancy for these three types of patients (A, B, and C). We observe that by increasing the storage redundancy, a patient with high severity real SNPs gains more privacy than a patient with lower severity real SNPs, hence the storage redundancy can be customized for each patient differently based on the types of his real SNPs. It can be argued that the amount of storage redundancy for a patient can leak information (to the curious party the SPU) about the severities of his real SNPs. However, the severity of the SNPs is not the only criteria to determine the storage redundancy for a desired level of genomic privacy as we discuss next.

Finally, we study the relationship between the severity of the real SNPs, the number of LD pairs per SNP (number of SNPs with which a particular SNP has LD, i.e., k), and the storage redundancy. We assign the Vi values of the real SNPs (in $Y_P$) following a uniform distribution between 0 and 1. We set the LD parameters as $\mu(l)=0.8$, $\sigma(l)=0.25$, $\mu(k)=2$, and $\sigma(k)=1.5$. Then, we observe and compare the following potential scenarios in different types of patients: (i) The real low severity SNPs of the patient (i.e., his real SNPs with low Vi values) have a higher number of LD pairs (i.e., higher k values) with respect to his high severity real SNPs (we note that, in all cases, k values are obtained from the same truncated Gaussian distribution with $\mu(k)=2$, and $\sigma(k)=1.5$); (ii) k values are assigned randomly to the SNPs; and (iii) the real high severity SNPs of the patient (i.e., his real SNPs with high $V_i$ values) have a higher number of LD pairs (i.e., higher k values) with respect to his low severity real SNPs. Again, we set a patient's genomic privacy to 100% when the storage redundancy is maximum at the SPU (as in Method 1 in Section 2.3). We illustrate our results in FIG. 8, and show different storage redundancy requirements for different types of patients (to provide the same level of privacy). For example, to achieve 40% genomic privacy, the SPU requires 400% storage redundancy for a patient whose less severe real SNPs have more LD pairs, whereas it requires 600% storage redundancy for another patient whose more severe real SNPs have more LD pairs (which means more storage per patient, as discussed in Section 3.1). This result also supports our belief to customize the storage redundancy for each patient.

We obtained similar patterns for further variations of the variables but we do not present these results due to the space limitation. In summary, depending on the actual $\mu(k)$, $\sigma(k)$, $\mu(l)$, $\sigma(l)$, and $V_i$ values (which will be determined as a result of the medical research), the storage redundancy can be determined (and customized for each patient based on the types of his variations) for this approach to keep the genomic privacy of the patient at a desired level. Note that the curious party at the SPU cannot infer the real SNPs of the patient (or the severities of the patient's real SNPs) from the amount of customized storage redundancy, because the storage redundancy (for a desired level of genomic privacy) depends on various factors. For example, a patient with low storage redundancy (for a desired level of genomic privacy) could mean that (i) he carries mostly low severity real SNP (as in FIG. 7), (ii) he carries mixed severity real SNPs, but his less severe real SNPs have more LD pairs (as in FIG. 8), (iii) his real SNPs (regardless of their severities) have low number of LD pairs (as in FIG. 3), or (iv) his real SNPs (regardless of their severities) have low LD strengths (as in FIG. 4).

2.5 Method 3

Encrypted Locations at the SPU

Let $L^P = \{L_i : i \in Y_P\}$ represent the set of locations (on the DNA sequence) of the patient P's real SNPs (in $Y_P$). As opposed to the previous two approaches, here, we propose to encrypt the locations of the SNPs along with their contents. By doing so, we save storage costs by storing only the real SNPs in $Y_P$ at the SPU (around 4 million) while providing the highest level of privacy (as in Section 2.3). These benefits, however, come with a cost in the practicality of the algorithm, introducing extra steps for the patient (P) during the protocol. Although we can assume that these extra steps can easily be handled via the patient's device such as smart card or mobile device, this approach still requires more message exchanges (as will be described next) between the parties, compared to the previous two approaches.

In some environments, dividing the weak private of the patient, and distributing two shares of the weak private key to the SPU and MU might not be acceptable (e.g., when it is likely that the SPU and MU will collaborate to retrieve patient's weak private). Therefore, for the sake of completeness, in the following, we present Method 3 with and without proxy encryption (i.e., without distributing the patient's private key to other parties). The Method 1 and Method 2 can also be modified similarly to avoid proxy encryption.

2.5.1 With Proxy Encryption

The initial steps of the protocol are the same as in Section 2.3, except for Steps 2 and 3 in which the locations of the SNPs are encrypted and a Bloom filter [39] is generated. Below, we summarize the different steps of this approach (the unchanged steps are not repeated). These steps are illustrated in FIG. 9.

Step 2: The Certified Institution (CI) first determines the locations of P's real SNPs (in $Y_P$) and constructs $L^P$. Then, the CI constructs a Bloom filter using the elements of $L^P$ as inputs.

A Bloom filter is a simple space-efficient randomized data structure for representing a set in order to support membership queries [39]. A Bloom filter for representing a set $L^P$ is described by an array of κ bits, initially all set to 0. It employs independent hash functions $H_1, \ldots H_\gamma$ with range $\{1, \ldots, \kappa\}$. For every element $L_i \in L^P$, the bits $H_1(L_i), \ldots, H_\gamma(L_i)$ in the array are set to 1. A location can be set to 1 multiple times, but only the first change has an effect.

After constructing the Bloom filter, the CI encrypts each element in $L^P$ by using a symmetric key shared between the CI and P (established during Step 0 as in Section 2.3) and generates $L^P_E = \{E(L_i): i \in Y_P\}$. The CI also encrypts a dummy variant (representing the potential SNPs in $\Omega_P$) along with the real SNPs of the patient (using P's public key). Furthermore, the CI associates a dummy position $L_0$ for this dummy variant and encrypts $L_0$ using the symmetric key between the CI and P to obtain the encrypted dummy position $E(L_0)$.

Step 3: The CI sends the constructed Bloom filter and the encrypted dummy position $E(L_0)$ to the patient for storage into the patient device, and encrypted SNPs and locations to the SPU.

Step 6: The MU tells the patient the locations of the SNPs that are required for the susceptibility test or requested directly as the relevant SNPs.

Step 7: The patient inputs each requested location $L_j$ to the Bloom filter to determine if the corresponding location is stored at his Bloom filter (i.e., to determine if he has a real SNP at the corresponding location).

To check if $L_j$ belongs to $L^P$, the patient checks whether all $H_1(L_j), \ldots, H_\gamma(L_j)$ are set to 1. If not, $L_j$ definitely does not belong to $L^P$. Otherwise, the patient assumes $L_j \in L^P$, although this may be wrong with some probability. That is, a Bloom filter could yield a false positive, where it suggests that $L_j$ is in $L^P$ even though it is not. This probability can be decreased at the expense of increasing Bloom filter length (i.e., κ). Further, the false positive probability can be significantly reduced by using some proposed techniques such as [40, 41]. As a result of this process (a) If the location is in his Bloom filter (i.e., if he has a real SNP at the corresponding location), P encrypts the location with the symmetric key between the CI and P.

(b) If the location is not in his Bloom filter (i.e., if he does not have a real SNP at the corresponding location), P uses $E(L_0)$ as the encrypted location.

We note that the above operations can be easily done via the patient's device (e.g., by reading the patient's device at the MU as a consent to the test) or mobile device (e.g., by consenting via a smart phone application) by using the stored Bloom filter output, $E(L_0)$, and symmetric key between the CI and P.

Step 8: The patient sends the SPU the encrypted locations of the SNPs which will be provided to the MU.

Step 9: The encrypted SNPs are sent to the MU in the same order as they are requested in Step 6.

(a) If only the end-result is requested, the corresponding SNPs are re-encrypted at the SPU under the patient's public key (re-encryption under the same public key is discusses in Section 2.1). As there is only one value stored at the SPU representing the contents of the potential SNPs at which P does not have a variant (at position $E(L_0)$), this value is re-encrypted for each different request of a non-variant, so that the MU cannot infer the locations of the non-variants of the patient.

(b) If relevant SNPs are requested, the SPU partially decrypts the relevant SNPs by using a part of P's private key following a proxy encryption protocol (Section 2.1).

Step 10: Re-encrypted (or partially decrypted) SNPs are sent to the MU by the SPU.

Step 11: One of the following two scenarios occur at the MU: (a) If only the end-result is requested, the MU computes P's total susceptibility to disease X by using the homomorphic properties of the Paillier cryptosystem (similar to the discussion in Section 2.6) under the patient's public key. Although the discussion in Section 2.6 is held considering Method 1 (or Method 2), a similar technique is used for this approach at the MU, hence we do not discuss it again.

(b) If relevant SNPs are requested, the MU decrypts the message received from the SPU by using the other part of P's private key and recovers the relevant SNPs.

Step 12: The MU sends the encrypted end-result to the SPU.

Step 13: The SPU partially decrypts the end-result using a part of P's private key by following a proxy encryption protocol (Section 2.1) and sends it back to the MU.

Step 14: The MU decrypts the message received from the SPU by using the other part of P's private key and recovers the end-result.

2.5.2 Without Proxy Encryption

In this approach, the SPU stores only the encrypted SNPs and encrypted locations. Genomic data encrypted by P's public key is only decrypted at P, and the weak private key of P remains only at P (i.e., shares of the weak private key are not distributed to the SPU or MU). Most of this approach is the same as Method 3 with proxy encryption. Indeed, the first 8 steps of the algorithm are the same, except for the distribution of parts of P's private key. The only difference is the transfer of the end-result or the relevant SNPs to the MU as follows:

If the relevant SNPs are requested by the MU, the SPU sends the encrypted SNPs (by P's public key) to P. P decrypts these SNPs (using his weak private key) and sends them to the MU.

If the end-result of the susceptibility test is requested by the MU, the disease-susceptibility test is done (via homomorphic operations) at the MU and the encrypted end-result is sent to P. Then, P decrypts the end-result and sends it back to the MU.

We note that the security of the communication between P and the MU is provided by symmetric keys as discussed before. The above operations put some more burdens on the patient during the protocol. However, we emphasize that these operations can be smoothly done on the patient's device without requiring a substantial effort from the patient himself.

In summary, as the locations of the real SNPs are encrypted, a curious party at the SPU cannot infer the contents of the SNPs from their locations (as in Section 2.3), hence it is enough to store only the real SNPs in $Y_P$. Furthermore, the privacy provided by this approach (with or without proxy encryption) is the same as 900% redundancy in Method 2 (i.e., similar to Method 1), hence we do not discuss it again. Another advantage of this approach (i.e., Method 3 in general) is that individual contributions of the genetic variant markers remain secret at the MU, because the homomorphic operations are conducted at the MU. This advantage might become more significant when this approach is used for personalized medicine methods in which the pharmaceutical company (embodied in this case as the medical unit) does not want to reveal the genetic properties of its drugs. Thus, if introducing the described extra steps for the patient and few additional message exchanges between the parties are tolerated, this approach operates with relatively modest storage and yet provides very good privacy.

2.6 Computing Disease Susceptibility Via Homomorphic Operations

We now present the disease-susceptibility test via homomorphic operations at the SPU for Method 1 (Section 2.3) and Method 2 (Section 2.4). Similar techniques can be used for Method 3 at the MU, as discussed in Section 2.5.

The SPU uses a proper function to compute P's predicted disease susceptibility via homomorphic encryption. There are different functions for computing the predicted susceptibility. In [25], focusing on one example of many diseases that require a susceptibility test involving multiple SNPs, Kathiresan et al. propose to count the number of unfavorable alleles carried by the patient for each SNP related to a particular disease. Similarly, in [26], Ashley et al. propose to multiply the Likelihood Ratios (LRs) of the most important SNPs for a particular disease in order to compute a patient's predicted susceptibility. LR values are determined as a result of medical studies. Furthermore, a weighted averaging function can also be used, which computes the predicted susceptibility by weighting the contributions of SNPs by their contributions (e.g., LR values of the SNPs). Note that our proposed privacy-preserving mechanisms are not limited by the types of the functions (used to test the disease susceptibility). It is expected that these functions will evolve over time; hence the proposed algorithms can be developed to keep up with this evolution.

In the following, we discuss how to compute the predicted disease susceptibility at the SPU by using a toy example to show how the homomorphic encryption is used at the SPU. Initially, we assume that the function at the SPU is weighted averaging (which is an advanced version of the function proposed in [25]) and show how the predicted susceptibility is computed using encrypted SNPs. Then, we show how the function proposed in [26] (i.e., multiplication of LR values) can be utilized at the SPU.

2.6.1 Weighted Averaging

Assume that (for simplicity) the susceptibility to disease X is determined by the set of SNPs $\Omega=\{SNP_m, SNP_n\}$, which occur at particular locations of the DNA sequence. $SNP_m^P$ and $SNP_n^P$ are not necessarily among the real SNPs of the patient P (i.e., P does not need to have a variant at those locations). The contributions of different states of $SNP_i^P$ for $i \in \{m, n\}$ to the susceptibility to disease X are computed via previous studies (on case and control populations) and they are already known by the MU. That is, $p_0^i(X) \square Pr(X|SNP_i^P=0)$ and $p_1^i(X) \square Pr(X|SNP_i^P=1)$ ($i \in \{m, n\}$) are determined and known by the MU. Further, the contribution (e.g., LR value) of $SNP_i$ to the susceptibility to disease X is denoted by $C_i^X$. Note that these contributions are also computed by previous studies on case and control groups and they are known by the MU.

As we have discussed before, the SPU stores the set of SNPs of the patient P, encrypted by P's public key (n, g, h=$g^x$). Encryption is done using the modified Paillier cryptosystem as discussed in Section 2.1. Thus, the SPU uses $E(SNP_m^P, g^x)$ and $E(SNP_n^P, g^x)$ for the computation of predicted susceptibility of P to disease X. From now on, we drop the r values in the above encrypted messages for the clarity of the presentation (r values are chosen randomly from the set [1, n/4] for every encrypted message as discussed in Section 2.1). Similarly, the MU provides the following to the SPU in plaintext: (i) the markers for disease X ($SNP_m$ and $SNP_n$), (ii) corresponding probabilities $p_j^i(X)$, $i \in \{m,n\}$ and $j \in \{0,1\}$, and (iii) the contributions of each SNP $C_i^X$.

Next, the SPU encrypts j ($j \in \{0,1\}$) using P's public key to obtain $E(0, g^x)$ and $E(1, g^x)$ for the homomorphic computations. This encryption can also be done at the MU and sent to the SPU. Alternatively, we might assume that SNPs of a patient are stored at the SPU in pairs of $\{E(|SNP_i^P-0|, g^x), E(|SNP_i^P-1|, g^x)\}$ for each $SNP_i^P$, instead of the actual values of the SNPs. In this case, the above encryption at the SPU would not be required.

The SPU computes the predicted susceptibility of the patient P to disease X by using weighted averaging.

This can be computed in plaintext as below:

$$S_P^X = \frac{1}{C_m^X + C_n^X} \times \sum_{i \in m,n} C_i^X \left\{ \frac{P_0^i(X)}{(0-1)}[SNP_i^P - 1] + \frac{P_1^i(X)}{(1-0)}[SNP_i^P - 0] \right\}. \quad (9)$$

The computation in (9) can be realized using the encrypted SNPs of the patient (and utilizing the homomorphic properties of the Paillier cryptosystem) to compute the encrypted disease susceptibility, $E(S_P^X, g^x)$ as below:

$$E(S_P^X, g^x) = \left\{ \prod_{i \in \{m,n\}} \left\{ \begin{array}{l} [E(SNP_i^P, g^x)E(1, g^x)^{-1}]^{\Delta_i^1} \times \\ [E(SNP_i^P, g^x)E(0, g^x)^{-1}]^{\Delta_i^2} \end{array} \right\}^{C_i^X} \right\}^\theta, \quad (10)$$

where $$\Delta_i^1 = \frac{P_0^i(X)}{0-1}, \quad (11a)$$

$$\Delta_i^2 = \frac{P_1^i(X)}{1-0}, \quad (11b)$$

$$\Theta = \frac{1}{C_m^X + C_n^X}. \quad (11c)$$

We note that the end-result in (10) is encrypted by P's public key.

Then, the SPU partially decrypts the end-result $E(S_P^X, g^x)$ using its share ($x^{(1)}$) of P's private key (x) as discussed in Section 2.1 to obtain $E(S_P^X, g^{x^{(2)}})$ and sends it to the MU. Finally, the MU decrypts $E(S_P^X, g^{x^{(n)}})$ using its share ($x^{(2)}$) of P's private key to recover the end-result $S_P^X$.

In some genetic tests, the types of the real SNPs (e.g., homozygous or heterozygous) become also important. In this case, $SNP_i^P$ can take three different values from the set $\{0, 1, 2\}$ to represent a potential SNP (i.e., nonvariant), a real homozygous SNP, and a real heterozygous SNP, respectively. In such a scenario, to conduct the disease-susceptibility test via homomorphic operations, the SPU should store the squared values of the SNPs. That is, for each $SNP_i^P$ of the patient P, the SPU should store $E((SNP_i^P)^2, g^x)$. Depending on the types of genomic tests that would be supported by the SPU (and the functions required for these tests), the format of storage of patient's SNPs can be determined beforehand, and SNPs can be stored accordingly just after the sequencing process.

2.6.2 Likelihood Ratio Test

We now assume that the predicted disease susceptibility is computed from the multiplication of Likelihood Ratios (LRs) of the corresponding SNPs as in [26] and show how such a computation would be handled at the SPU by using homomorphic operations.

In this approach, the predicted disease susceptibility is computed by multiplying the initial risk of the patient (e.g., for disease X) by the LR value of each SNP related to that disease (LR value of a SNP i depends on the value of $SNP_i^P$ at the patient P). The initial risk of the patient P for the disease X is represented as $I_X^P$. We note that $I_X^P$ is determined by considering several factors (other than patient's genomic data) such as patient's age, gender, height, weight, and environment. Thus, this initial risk can be computed directly by the MU. We also note that if the LR value corresponding to a particular SNP is less than one, the risk for the disease decreases. Otherwise, if the LR value is greater than one, the risk increases for the corresponding disease.

Similar to before, we assume that the susceptibility to disease X is determined by the set of SNPs in $\Omega=\{SNP_m, SNP_n\}$. We denote the LR values due to $SNP_i^P=0$ and $SNP_i^P=1$ for disease X as $L_X^i(0)$ and $L_X^i(1)$, respectively.

The SPU stores the SNPs of the patient P, encrypted by P's public key. The MU sends the following to the SPU: (i)

$L_X^i(j)$ values (i∈{m,n} and j∈{0,1}) in plaintext, and (ii) the markers for disease X. The MU also encrypts the log of initial risk value, $\ln(I_X^P)$, by P's public key and sends $E(\ln(I_X^P), g^x)$ to the SPU. Alternatively, the contribution of the initial risk to the disease susceptibility can be included to the end-result at the end, at the MU.

The Paillier cryptosystem does not support multiplicative homomorphism in ciphertext (it only supports the multiplication of a ciphertext with a constant as discussed in Section 2.1). Thus, instead of multiplying the LR values, we propose using addition in log-domain at the SPU. Thus, the SPU computes the predicted susceptibility of P to disease X as below:

$$E(\ln(S_P^X), g^x) = E(\ln(I_P^X), g^x) \times \prod_{i \in m,n} \left\{ [E(SNP_i^P, g^x) \cdot E(1, g^x)^{-1}]^{\Xi_i^1} \times \right.$$
$$\left. [E(SNP_i^P, g^x) \cdot E(0, g^x)^{-1}]^{\Xi_i^2} \right\} \quad (12)$$

where $$\Xi_i^1 - \frac{\ln(L_X^i(0))}{(0-1)} \quad (13a)$$

$$\Xi_i^2 - \frac{\ln(L_X^i(1))}{(1-0)} \quad (13b)$$

We note that (12) corresponds to the below computation in plaintext:

$$\ln(S_P^X) = \quad (14)$$
$$\ln(I_X^P) + \sum_{i \in m,n} \left\{ [SNP_i^P - 1] \times \frac{\ln(L_X^i(0))}{(0-1)} + [SNP_i^P - 0] \times \frac{\ln(L_X^i(1))}{(1-0)} \right\}.$$

As before, the SPU partially decrypts $E(\ln(SX\ P), g^x)$ using $x(1)$ (its share of P's private key) to obtain $E(\ln(S_P^X), g^{x^{(2)}})$ and sends it to the MU. Finally, the MU decrypts $E(\ln(S_P^X), g^{x^{(2)}})$ using $x^{(2)}$ (its share of P's private key) to recover $\ln(S_P^X)$, and computes $e^{(\ln(S_PX))}$ to obtain $S_P^X$. Similar to weighted averaging, if the types of the real SNPs are used for the test (in which there are three possible states for $SNP_i^P$, squared values of the SNPs should be stored at the SPU for each patient.

2.6.3 Use of Structural Variations

In this section, we describe how the method proposed in Section 2.6.1 for computing disease susceptibility based on weighted averaging can be extended beyond the use of SNPs. A similar approach can be used to also extend the likelihood ratio test as proposed in Section 2.6.2. We consider the case of more complex human genetic variations that involve multiple nucleotides (SNPs involve just a single nucleotide) such as insertions, deletions, copy number variants, and inversions. These variations are more generally referred as "structural" variations (SVs) [43]. Note that Method 0, Method 1, Method 2 and Method 3 described respectively in Sections 2.2, 2.3, 2.4, and 2.5 can be used with SVs without any further change. Only the disease susceptibility computation changes.

Insertions and deletions (jointly called "INDELs") are a specific type of SVs consisting of an insertion or a deletion of one or multiple contiguous nucleotides with respect to the reference genome. INDELs can determine the susceptibility or resistance to diseases susceptibility. For example, INDEL "rs333", that is a 32 nucleotides deletion in the CCR5 gene, protects against HIV.

Copy number variants (CNVs) consist of a segment of DNA (several contiguous nucleotides) that is present at a variable copy number in comparison with a reference genome. Some CNV can be associated with diseases. For example, a higher copy number for the EGFR gene can be associated with lung cancer while a higher copy number for CCL3L1 gene can been associated with lower susceptibility to HIV infection [44,45].

Inversions are segment of DNA that are reversed in orientation with respect to the reference genome. Like INDELs and CNVs, also inversions can be associated with diseases. One of the best-characterized recurrent inversions giving rise to disease causes haemophilia A [46].

Differently from SNPs that are mostly bi-allelic (i.e., they have two alleles or versions at a given SNP position), SVs can often be multi-allelic (i.e., they have more than two alleles at a given SV position; for example, for a CNV different copy numbers represent different alleles and there can be multiple copy numbers at a given CNV position).

In the case of a bi-allelic SVs, we can treat them as SNPs. Hence, we can assume that $SV_i$ at the patient P is represented as $SV_i^P$ and $SV_i^P=1$, if P has a real SV (i.e., a variant) at this location, and $SV_i^P=0$, if P does not have a variant at this location. The disease susceptibility can then be computed as discussed in Sections 2.6.1 and 2.6.2.

In the case of multi-allelic SVs, different alleles might have a different impact on the susceptibility or resistance to a disease. Hence, a case-by-case assessment is needed to know which allele has a given patient. We can assume that $SV_i^P=k_i$, if P has a real SV (i.e., a variant) at this location with the allele $k_i$, and $SV_i^P=0$, if P does not have a variant at this location (i.e., his sequence is the same as the reference sequence in that position). We assume $k_i$ is a number from 1 to $\mu_i$, where $\mu_i$ is the total number of alleles for $SV_i$. Then, the disease susceptibility can be computed as follows.

Similarly to the case of SNPs, we assume that the susceptibility to disease X is determined by the set of SVs $\Lambda=\{SV_m, SV_n\}$. Assume also that a specific allele $k_i$ of $SV_i$, for $i \in \{m, n\}$, is associated to the susceptibility to disease X and its contribution is computed by previous studies and known by the MU. That is, $p_k^i(X)=Pr(X|SV_i^P=k_i)$ and $p_{\overline{k}}^i(X)=Pr(X|SV_i^P \neq k_i)$ is determined and known by the MU. Contribution of $SV_i$ to susceptibility to disease X is denoted by $C_i^X$ as explained in Section 2.6.1.

The SPU stores the SVs of the patient P, encrypted by P's public key. The MU sends the following to the SPU: (i) markers for disease X $(SV_m, SV_n)$, (ii) the allele associated with X encrypted with P's public key $E(k_i, g^x)$, $i \in \{m, n\}$, (iii) the corresponding probabilities $p_k^i(X)$ and $p_{\overline{k}}^i(X)$, $i \in \{m, n\}$, and (iv) the contributions of each SVs $C_i^X$. Next, the SPU computes the encrypted susceptibility of patient P to disease X by using weighted averaging as below:

$$E(S_P^X, g^x) = \quad (1)$$
$$\left\{ \prod_{i \in [m,n]} \left\{ \begin{array}{l} [f_e(E(SV_i^P, g^x), E(k_i, g^x)^{-1}]^{\Delta_i^{\overline{k}}} \times \\ [f_e(E(SV_i^P, g^x), E(k_i, g^x)E(0, g^x)^{-1}]^{\Delta_i^k} \end{array} \right\}^{C_i^X} \right\}^\Theta$$

where

-continued $$\Delta_i^{\bar{k}} = \frac{p_{\bar{k}}^i(X)}{0-1}, \quad (2a)$$

$$\Delta_i^k = \frac{p_k^i(X)}{1-0}, \quad (2b)$$

$$\Theta = \frac{1}{C_m^X + c_n^X}, \quad (2c)$$

and $f_e(E(a,g^x),E(b,g^x))$ is a secure equality function that takes as input two l bits integers encrypted with the same key $E(a,g^x)$ and $E(b,g^x)$, and outputs $E(0, g^x)$ if $a \neq b$ and $E(1,g^x)$ if $a=b$. In particular, the proposed secure equality function is computed as follows:

$$f_e(E(a,g^x),E(b,g^x)) = f_c(E(a,g^x),E(b,g^x)) \times f_c(E(b,g^x),E(a,g^x)) \times E(1,g^x)^{-1} \quad (3)$$

where $f_c(E(a,g^x),E(b,g^x))$ is a secure comparison protocol adapted from [47] that takes the same inputs as $f_e$ and outputs $E(1,g^x)$ if $a \le b$ and $E(0, g^x)$, otherwise. The secure comparison function $f_c$ is described in detail in Algorithm 1.

We note that (1) corresponds to the below computation in plaintext:

$$S_P^X = \frac{1}{C_m^X + c_n^X} \times \Sigma_{i \in \{m,n\}} \quad (4)$$

$$C_i^X \left\{ \frac{p_{\bar{k}}^i(X)}{0-1} [(SV_i^p = k_i) - 1] + \frac{p_k^i(X)}{1-0} [(SV_i^p = k_i) - 0] \right\}.$$

As before, the SPU partially decrypts $E(S_P^X,g^x)$ using $x^{(1)}$ (its share of P's private key) to obtain $E(S_P^X, g^{x^{(2)}})$ and sends it to the MU. Finally, the MU decrypts $E(S_P^X,g^{x^{(2)}})$ using $x^{(2)}$ (its share of P's private key) to recover $S_P^X$. We note that a similar technique can be used to computed disease susceptibility through likelihood ratio test, hence we do not discuss it again. As also discussed in Section 2.6.1, depending on the type of genetic test, the format of storage of patient's SVs can be determined beforehand, and SVs can be stored accordingly just after the sequencing process.

3 Evaluation and Implementation of the Proposed Methods

In FIG. 10, based on the discussion in the previous sections, we graphically compare the proposed methods considering the level of privacy they provide, their practicality (for the patient), and their storage requirements (at the SPU). In this section, we report our findings about the complexity and security of the proposed methods.

3.1 Implementation and Complexity Evaluation

To evaluate the practicality of the proposed privacy-preserving algorithms, we implemented them, and assessed their storage requirements and computational complexities on Intel Core i7-2620M CPU with 2.70 GHz processor under Windows 7 Enterprise 64-bit Operating System. We set the size of the security parameter (n in Paillier cryptosystem in Section 2.1) to 1024 bits. We computed the disease susceptibility using weighted averaging (at the SPU or MU, see Section 2.6.1 as well as LR test in Section 2.6.2 which also has similar complexity) and real SNP profiles from [42]. Our implementation relies on a MySQL 5.5 database managed by the open source tool MySQL Workbench. To provide a platform-independent implementation, we used the Java programming language along with the open-source Integrated Development Environment, NetBeans IDE 7.1.1., for the implementation of the Java code. We note that our code for the implementation is not optimized, and better results can be expected with an optimized implementation.

In Table II, we summarize the computational and storage complexities of the proposed methods at (i) Certified Institution (CI), (ii) SPU, (iii) MU, and (iv) P. We evaluate the proposed methods considering the following costs: (i) encryption of patient's variants, (ii) disease-susceptibility test at the SPU via homomorphic operations (using ten variants), (iii) decryption of the end-result (or relevant SNPs), (iv) proxy encryption, and (v) storage costs, in which B represent the percentage of storage redundancy at the SPU. We did not explicitly implement the Bloom filter (for Method 3) and symmetric encryption/decryption between Algorithm 1

Secure Comparison $f_c$ ($E(a, g^x)$, $E(b, g^x)$)

Input: @ SPU: $E(a, g^x)$, $E(b,g^x)$ and $x^{(1)}$. @ MU: $x^{(2)}$.
Output: @ SPU: $f_c$ ($E(a, g^x),E(b, g^x)$) = $E((a \le b), g^x)$. @ MU: $\perp$.
// Let a and b be two l-bit integers
1: SPU computes $E(z, g^x) \leftarrow E(a, g^x) * E(b, g^x)^{-1} * E(2^l, g^x) = E(a - b + 2^l, g^x)$.
2: SPU generates a random number r, $0 \le r < n^2$, and blinds $E(z, g^x)$:
   $E(z, g^x) \leftarrow E(\hat{z}, g^x) \times E(r, g^x) = E(z + r, g^x)$.
3: SPU partially decrypts $E(\hat{z}, g^x)$ with $x^{(1)}$ and sends $E(z, g^{x^{(2)}})$ to MU
4: MU decrypts $E(\hat{z}, g^{x^{(2)}})$ with $x^{(2)}$ and obtains $\hat{z}$
5: MU computes $\beta \leftarrow \hat{z} \mod 2^l$.
6: SPU computes $\alpha \leftarrow r \mod 2^l$.
7: SPU and MU run a DGK or a modified DGK comparison with private inputs $\alpha$ and $\beta$ and obtain
   $\delta_{SPU}$ (@ SPU) and $\delta_{MU}$ (@ MU) as described in [6].

8: MU computes $\dfrac{\hat{z}}{2^l}$ and sends $E\left(\dfrac{\hat{z}}{2^l}, g^x\right)$ and $E(\delta_{MU}, g^x)$ to SPU.

9: SPU computes $E((\beta < \alpha), g^x)$:
   if $\delta_{SPU} = 1$ then $E((\beta < \alpha), g^x) \leftarrow E(\delta_{MU}, g^x)$,
   else $E((\beta < \alpha), g^x) \leftarrow E(1, g^x) \times E(\delta_{MU}, g^x)^{-1}$.

10: SPU computes $E((a < b), g^x) \leftarrow E\left(\dfrac{z}{2^l}, g^x\right) \times \left[E\left(\dfrac{r}{2^l}, g^x\right) \times E((\beta < \alpha), g^x)\right]^{-1}$ the parties for the security of the communication. However, the computational costs due to these operations are negligible compared to Paillier encryption/decryption and homomorphic operations.

We emphasize that the encryption of the variants at the CI is a one-time operation and is significantly faster than the sequencing and analysis of the sequence (which takes days). Further, this encryption can be conducted much more efficiently by computing some parameters, such as $(g^r, h^r)$ pairs, offline for various r values, for each patient. Indeed, by computing $(g^r, h^r)$ pairs offline, we observe that the encryption takes only 0.017 ms per variant at the CI.

putational hardness assumption about a certain problem involving discrete logarithms in cyclic groups) in $Z^*_{n^2}$ holds, then the modified Paillier cryptosystem is semantically secure.

Finally, if the weak private key of the patient, x, is randomly divided and distributed to the Storage and Processing Unit (SPU) and Medical unit (MU) as in Method 1, this weak private key could be revealed if the MU colludes with the SPU, but the factors n, p, and q remain secret. We note that such a collusion is not considered in this study. However, for the sake of completeness, in Section 2.5.2, we present an alternative approach (Method 3 without proxy

TABLE 2

Computational and Storage Complexities of the Proposed Methods

| Method 1 and Method 2 | | | | |
|---|---|---|---|---|
| @ CI | | | @ SPU | @ MU |
| Paillier Encryption | Homomorphic Operations | Proxy Encryption | Storage | Paillier Decryption |
| 30 ms./variant | 1 sec. (10 variants) | 2 ms. | $500 \times \left(1 + \frac{\phi}{100}\right)$ MB/patient | 26 ms. |

| Method 3 with proxy encryption | | | | |
|---|---|---|---|---|
| @ CI | | @ SPU | | @ MU |
| Paillier Encryption | Proxy Encryption | Storage | Homomorphic Operations | Paillier Decryption |
| 30 ms./variant | 2 ms. | 500 MB/patient | 1 sec. (10 variants) | 26 ms. |

| Method 3 without proxy encryption | | | |
|---|---|---|---|
| @ CI | @ SPU | @ MU | @ P |
| Paillier Encryption | Storage | Homomorphic Operations | Paillier Decryption |
| 30 ms./variant | 500 MB/patient | 1 sec. (10 variants) | 26 ms. |

It is also possible to conduct private statistical tests (by a medical researcher) on the data stored at the SPU in order to get statistics about the variants of multiple patients. Conducting such a statistical test for a variant (about its type) on 100K patients takes around 55 minutes at the SPU and scales linearly with the number of patients. Note that such a statistical test is only possible with Method 1 or Method 2; using Method 3 and querying the encrypted locations of SNPs from 100K patients is not practical for this application.

In summary, all these numbers show the practicality of our privacy-preserving algorithms.

3.2 Security Evaluation

The proposed schemes preserve the privacy of patients' genomic data relying on the security strength of modified Paillier cryptosystem (in Section 2.1). The extensive security evaluation of the modified Paillier cryptosystem can be found in [33]. Below we summarize two important security features of this cryptosystem.

One-wayness: This property means that no efficient adversary has any significant chance of finding a preimage to the ciphertext when he sees only the ciphertext and the public key of the patient. It is shown in [33] that the one-wayness of the modified Paillier cryptosystem can be related to the Lift Diffie-Hellman problem which is shown to be as hard as the partial Discrete Logarithm problem.

Semantic security: This property ensures that an adversary will be unable to distinguish pairs of ciphertexts based on the message they encrypt. It is shown in [33] that if Decisional Diffie-Hellman Assumption (a comencryption) that avoids distributing the patient's weak private key to other parties, hence is robust against such a collusion.

The invention is also related to a computer readable storage medium having recorded thereon a computer program for processing genomic data of a patient and performing the steps of any of the method claims.

REFERENCES

[1] A. Cavoukian, "Privacy by design," 2009, http://www.ontla.on.ca/library/repository/mon/23002/289982.pdf.
[2] S. F. Gurses, "Multilateral privacy requirements analysis in online social network services," 2010, PhD thesis, K U Leuven.
[3] M. Langheinrich, "Principles of privacy-aware ubiquitous systems," Proceedings of Ubiquitous Computing (UbiComp), 2001.
[4] G. van Blarkom, J. Borking, and J. Olk, "Handbook of privacy and privacy-enhancing technologies (the case of intelligent software agents)," College bescherming persoonsgegevens, 2003.
[5] http://www.personalgenomes.org/consent/PGP Consent Approved 02212012. pdf.
[6] J. R. Troncoso-Pastoriza, S. Katzenbeisser, and M. Celik, "Privacy preserving error resilient DNA searching through oblivious automata," CCS '07: Proceedings of the 14th ACM Conference on Computer and Communications Security, pp. 519-528, 2007.
[7] M. Blanton and M. Aliasgari, "Secure outsourcing of DNA searching via finite automata," DBSec'10: Proceedings of the 24th Annual IFIP WG 11.3 Working Conference on Data and Applications Security and Privacy, pp. 49-64, 2010.

[8] S. Jha, L. Kruger, and V. Shmatikov, "Towards practical privacy for genomic computation," Proceedings of the 2008 IEEE Symposium on Security and Privacy, pp. 216-230, 2008.

[9] F. Bruekers, S. Katzenbeisser, K. Kursawe, and P. Tuyls, "Privacy-preserving matching of DNA profiles," Tech. Rep., 2008.

[10] M. Kantarcioglu, W. Jiang, Y. Liu, and B. Malin, "A cryptographic approach to securely share and query genomic sequences," IEEE Transactions on Information Technology in Biomedicine, vol. 12, no. 5, pp. 606-617, 2008.

[11] P. Baldi, R. Baronio, E. De Cristofaro, P. Gasti, and G. Tsudik, "Countering GATTACA: efficient and secure testing of fully-sequenced human genomes," CCS '11: Proceedings of the 18th ACM Conference on Computer and Communications Security, pp. 691-702, 2011.

[12] M. Canim, M. Kantarcioglu, and B. Malin, "Secure management of biomedical data with cryptographic hardware," IEEE Transactions on Information Technology in Biomedicine, vol. 16, no. 1, 2012.

[13] D. Eppstein, M. T. Goodrich, and P. Baldi, "Privacy-enhanced methods for comparing compressed DNA sequences," CoRR, vol. abs/1107.3593, 2011. [Online]. Available: http://arxiv.org/abs/1107.3593

[14] D. Eppstein and M. T. Goodrich, "Straggler identification in round-trip data streams via Newton's identities and invertible Bloom filters," IEEE Transactions on Knowledge and Data Engineering, vol. 23, no. 2, pp. 297-306, 2011.

[15] R. Wang, Y. F. Li, X. Wang, H. Tang, and X. Zhou, "Learning your identity and disease from research papers: information leaks in genome wide association study," CCS '09: Proceedings of the 16th ACM Conference on Computer and Communications Security, pp. 534-544, 2009.

[16] B. Malin and L. Sweeney, "How (not) to protect genomic data privacy in a distributed network: using trail re-identification to evaluate and design anonymity protection systems," Journal of Biomedical Informatics, vol. 37, pp. 179-192, June 2004.

[17] N. Homer, S. Szelinger, M. Redman, D. Duggan, and W. Tembe, "Resolving individuals contributing trace amounts of DNA to highly complex mixtures using high-density SNP genotyping microarrays," PLoS Genetics, vol. 4, August 2008.

[18] J. Gitschier, "Inferential genotyping of Y chromosomes in Latter-Day Saints founders and comparison to Utah samples in the HapMap project," Am. J. Hum. Genet., vol. 84, pp. 251-258, 2009.

[19] X. Zhou, B. Peng, Y. F. Li, Y. Chen, H. Tang, and X. Wang, "To release or not to release: evaluating information leaks in aggregate human-genome data," ESORICS'11: Proceedings of the 16th European Conference on Research in Computer Security, pp. 607-627, 2011.

[20] S. E. Fienberg, A. Slavkovic, and C. Uhler, "Privacy preserving GWAS data sharing," Proceedings of the IEEE 11th International Conference on Data Mining Workshops (ICDMW), December 2011.

[21] Y. Chen, B. Peng, X. Wang, and H. Tang, "Large-scale privacy-preserving mapping of human genomic sequences on hybrid clouds," NDSS'12: Proceeding of the 19th Network and Distributed System Security Symposium, 2012.

[22] R. Wang, X. Wang, Z. Li, H. Tang, M. K. Reiter, and Z. Dong, "Privacy-preserving genomic computation through program specialization," Proceedings of the 16th ACM Conference on Computer and Communications Security, pp. 338-347, 2009.

[23] R. Agrawal, A. Evfinnievski, and R. Srikant, "Information sharing across private databases," Proceedings of SIGMOD Conference, 2003.

[24] D. Dachman-Soled, T. Malkin, M. Raykova, and M. Yung, "Efficient robust private set intersection," Proceedings of the 7th International Conference on Applied Cryptography and Network Security, pp. 125-142, 2009.

[25] S. Kathiresan, O. Melander, D. Anevski, C. Guiducci, and N. Burtt, "Polymorphisms associated with cholesterol and risk of cardiovascular events," The New England Journal of Medicine, vol. 358, pp. 1240-1249, 2008.

[26] E. Ashley, A. Butte, M. Wheeler, R. Chen, and T. Klein, "Clinical assessment incorporating a personal genome," The Lancet, vol. 375, no. 9725, pp. 1525-1535, 2010.

[27] S. Seshadri, A. Fitzpatrick, M. A. Ikram, A. DeStefano, V. Gudnason, M. Boada, J. Bis, A. Smith, M. Carassquillo, J. Lambert, C. Consortium, G. Consortium, and E. Consortium, "Genome-wide analysis of genetic loci associated with Alzheimer disease," JAMA, vol. 303, pp. 1832-1840, 2010.

[28] http://www.ncbi.nInn.nih.gov/projects/SNP/.

[29] D. Greenbaum, A. Sboner, X. Mu, and M. Gerstein, "Genomics and privacy: Implications of the new reality of closed data for the field," PLoS Computational Biology, vol. 7, no. 12, 2011.

[30] M. Raykova, H. Zhao, and S. M. Bellovin, "Privacy enhanced access control for outsourced data sharing," Financial Cryptography and Data Security, 2012.

[31] M. T. Goodrich and M. Mitzenmacher, "Privacy-preserving access of outsourced data via oblivious RAM simulation," Proceedings of the 38th International Conference on Automata, Languages and Programming—Volume Part II, pp. 576-587, 2011.

[32] E. Stefanov, E. Shi, and D. Song, "Towards practical oblivious RAM," NDSS'12: Proceeding of the 19th Network and Distributed System Security Symposium, 2012.

[33] E. Bresson, D. Catalano, and D. Pointcheval, "A simple public-key cryptosystem with a double trapdoor decryption mechanism and its applications," Proceedings of Asiacrypt 03, LNCS 2894, pp. 37-54, 2003.

[34] M. Pirretti, P. Traynor, P. McDaniel, and B. Waters, "Secure attribute-based systems," Proceedings of the 13th ACM Conference on Computer and Communications Security, pp. 99-112, 2006.

[35] G. Ateniese, K. Fu, M. Green, and S. Hohenberger, "Improved proxy re-encryption schemes with applications to secure distributed storage," ACM Transactions on Information and System Security, vol. 9, pp. 1-30, February 2006.

[36] D. S. Falconer and T. F. Mackay, Introduction to Quantitative Genetics (4th Edition). Harlow, Essex, UK: Addison Wesley Longman, 1996.

[37] C. Diaz, S. Seys, J. Claessens, and B. Preneel, "Towards measuring anonymity," Proceedings of Privacy Enhancing Technologies Symposium (PETS), 2002.

[38] A. Serjantov and G. Danezis, "Towards an information theoretic metric for anonymity," Proceedings of Privacy Enhancing Technologies Symposium (PETS), 2002.

[39] B. H. Bloom, "Space/time trade-offs in hash coding with allowable errors," ACM Communications, vol. 13, no. 7, pp. 422-426, 1970.

[40] F. Hao, M. Kodialam, and T. V. Lakshman, "Building high accuracy Bloom filters using partitioned hashing," Proceedings of ACM International Conference on Measurement and Modeling of Computer Systems, pp. 277-288, 2007.

[41] P. S. Almeida, C. Baquero, N. Preguica, and D. Hutchison, "Scalable Bloom filters," Information Processing Letters, vol. 101, no. 6, pp. 255-261, 2007.

[42] The 1000 Genomes Project Consortium, "A map of human genome variation from population-scale sequencing," Nature, vol. 467, pp. 1061-1073, 2010.

[43] Sudmant, Peter H., Tobias Rausch, Eugene J. Gardner, Robert E. Handsaker, Alexej Abyzov, John Huddleston, Yan Zhang et al. "An integrated map of structural variation in 2,504 human genomes." Nature 526, no. 7571 (2015): 75-81.

[44] Cappuzzo, Federico, Fred R. Hirsch, Elisa Rossi, Stefania Bartolini, Giovanni L. Ceresoli, Lynne Bemis, Jerry Haney et al. "Epidermal growth factor receptor gene and protein and gefitinib sensitivity in non-small-cell lung cancer." Journal of the National Cancer Institute 97, no. 9 (2005): 643-655.

[45] Gonzalez, Enrique, Hemant Kulkarni, Hector Bolivar, Andrea Mangano, Racquel Sanchez, Gabriel Catano, Robert J. Nibbs et al. "The influence of CCL3L1 gene-containing segmental duplications on HIV-1/AIDS susceptibility." Science 307, no. 5714 (2005): 1434-1440.

[46] Lakich, Delia, Haig H. Kazazian, Stylianos E. Antonarakis, and Jane Gitschier. "Inversions disrupting the factor VIII gene are a common cause of severe haemophilia A." Nature genetics 5, no. 3(1993): 236-241.

[47] Veugen, Thijs. "Comparing encrypted data." Multimedia Signal Processing Group, Delft University of Technology, The Netherlands, and TNO Information and Communication Technology, Delft, The Netherlands, Tech. Rep (2011).

[48] Veugen, Thijs. "Improving the DGK comparison protocol." In Information Forensics and Security (WIFS), 2012 IEEE International Workshop on, pp. 49-54. IEEE, 2012.

The invention claimed is:

1. A method to process genomic data comprising the steps of:
associating, by a Certified Institution, a patient identification with a given patient;
generating, by the Certified Institution, a pair of asymmetric keys related to said patient comprising a private and a public key;
dividing, by the Certified Institution, the private key into at least a first and a second part;
storing, by the Certified Institution, the second part of the private key in a medical unit or in a patient device;
transmitting, by the Certified Institution, the first part of the private key to the Storage and Processing Unit;
analyzing, by the Certified Institution, an output of a Deoxyribonucleic Acid (DNA) sequencer and preparing an aligned genomic data for said patient comprising approved variants, such as Single Nucleotide Polymorphisms (SNPs) or structural variants (SVs), each approved variant representing a position in the genome and a value representing a nucleotide that varies between individuals;
extracting, by the Certified Institution, real and potential variants from said approved variants, said real and potential variants having each a position, said real variants being a subset of the approved variants and being different for each human being, said potential variants being the remaining part of the approved variants;
encrypting the value of each real variant and of at least some selected potential variants with the public key of the patient; and
sending the encrypted values with their respective positions and the patient identification to a Storage and Processing Unit.

2. The method of claim 1, further comprising:
selecting, by the Certified Institution, all or part of the potential variants;
analyzing, by the Certified Institution, the correlation between the selected potential variants and a privacy sensitivity of the real variants;
selecting, by the Certified Institution, a number of other potential variants, said number being determined according to the previous analysis and a level of privacy required.

3. The method of claim 1, further comprising the steps of:
generating, by the Certified Institution, a dummy variant comprising a dummy position and a dummy value, said dummy position being outside of the overall variant positions of a sequence;
encrypting, by the Certified Institution, the positions of the real variants with a symmetric key of the patient;
encrypting, by the Certified Institution, the dummy value with the public key of the patient;
encrypting, by the Certified Institution, the position of the dummy variant with the symmetric key of the patient;
sending, by the Certified Institution, to said Storage and Processing Unit, together with the encrypted variants, the dummy variant as well as the encrypted positions and the encrypted dummy position.

4. The method of claim 3, further comprising the steps of:
storing, by the Certified Institution, the position of the dummy variant into a patient device;
determining by the Certified Institution a set of positions which are common between the marker's position and the real variant's positions;
receiving by the Certified Institution from the medical unit an encrypted set of positions with the symmetric key of said patient, and for the marker's positions not present in the variant's position, dummy positions;
sending by the Certified Institution to the Storage and Processing Unit the encrypted marker's positions as well as the patient identification.

5. A method to process genomic data, said method comprising the steps of:
receiving by a Storage and Processing Unit encrypted values of real variants, such as Single Nucleotide Polymorphisms (SNP) or structured variants (SVs), for a patient, each real variant representing a position in the genome and a value representing a nucleotide that varies between individuals;
storing in the Storage and Processing Unit the encrypted values with their respective positions into the Storage and Processing Unit, as well as an identification of the patient;
receiving from a Certified Institution a first part of a private key of the patient, said private key comprising said first part and a second part, said second part being stored in a medical unit or in a patient device;
receiving by the Storage and Processing Unit from a medical unit genetic markers related to a personalized clinical test, the respective contributions of the related genetic markers and the patient identification of the patient;

retrieving by the Storage and Processing Unit the encrypted values for said patient matching the position of the genetic markers;

executing by the Storage and Processing Unit a genetic test by using the retrieved encrypted values, and the contribution of those markers thanks to homomorphic operations;

partially decrypting by the Storage and Processing Unit the result of the genetic test using said first part of the private key;

sending by the Storage and Processing Unit the partly decrypted result to a medical unit.

6. The method of claim 5, further comprising receiving by the Storage and Processing Unit encrypted values of at least some potential variants of said patient, said real and potential variants having each a position, said real variants being different for each human being, said potential variants being the remaining part of the approved variants.

7. The method of claim 5, further comprising the steps of retrieving by the Storage and Processing Unit, together with the encrypted variants, dummy variants encrypted with the public key of the patient, as well as positions of the real variant and of the dummy variants encrypted with a symmetric key of the patient.

8. The method of claim 5, further comprising receiving by the Storage and Processing Unit the allele associated with said genetic markers related to the personalized clinical test, and the corresponding probabilities.

\* \* \* \* \*